(12) United States Patent
Shimizu et al.

(10) Patent No.: US 6,269,690 B1
(45) Date of Patent: Aug. 7, 2001

(54) METHOD FOR ESTIMATING A TIRE WEAR LIFE

(75) Inventors: Akiyoshi Shimizu; Naoto Yamagishi; Hiroshi Mouri; Naohiro Sasaka, all of Kodaira; Hiroshi Kobayashi, Toyota; Tetsunori Haraguchi, Toyota; Kohshi Katoh, Toyota, all of (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 09/306,298

(22) Filed: May 6, 1999

(30) Foreign Application Priority Data

May 8, 1998 (JP) .................................................. 10-126176
May 8, 1998 (JP) .................................................. 10-126177
May 8, 1998 (JP) .................................................. 10-126179

(51) Int. Cl.[7] .................................................. G01M 17/02
(52) U.S. Cl. .............................................................. 73/146
(58) Field of Search ................. 73/146, 8, 9; 152/213 R, 152/213 A

(56) References Cited

U.S. PATENT DOCUMENTS

| 3,722,270 | 3/1973 | Sperberg ................................. 73/146 |
| 3,933,036 | 1/1976 | Lippmann et al. ..................... 73/146 |

FOREIGN PATENT DOCUMENTS

| 0 504 669 A | 9/1992 | (EP) . |
| 1-56374 | 11/1989 | (JP) . |
| 7-63658 | 3/1995 | (JP) . |

OTHER PUBLICATIONS

"A Trial on Laboratory Evaluation of Tire Wear," Yokohama Rubber Co, Japanese Automotive Engineers Society Fall lecture 1982 pp. 393–396. (No Month).

*Primary Examiner*—William Oen
(74) *Attorney, Agent, or Firm*—Oliff & Berridge, PLC

(57) ABSTRACT

The present invention provides a method for estimating a tire wear life which enables estimation of the tire wear life accurately in a short time. In this method, a rubber index Gi of a rubber test piece which is made of the same material as the material used in the tire tread portion of the tire whose tire wear life is to be estimated is measured using an abrasion tester which can be operated under a slip ratio of about 0.5 to 5% (step 100). Then, friction energies of the tire in free rolling, in a state in which the tire is provided with a toe angle, in a state in which a side force is applied to the tire, in a state in which a driving force is applied to the tire and in a state in which a braking force is applied to the tire are measured (step 102), respectively. An expected value of the tire wear life T1 is calculated from the rubber index Gi and the friction energies obtained above (step 104). The tire wear life is estimated from the expected value of the tire wear life T1 thus obtained (step 106).

32 Claims, 17 Drawing Sheets

□: EXPECTED VALUE OF WEAR PERIOD OBTAINED BY FORMULA (5)

▲: EXPECTED VALUE OF WEAR PERIOD OBTAINED BY FORMULA (7)

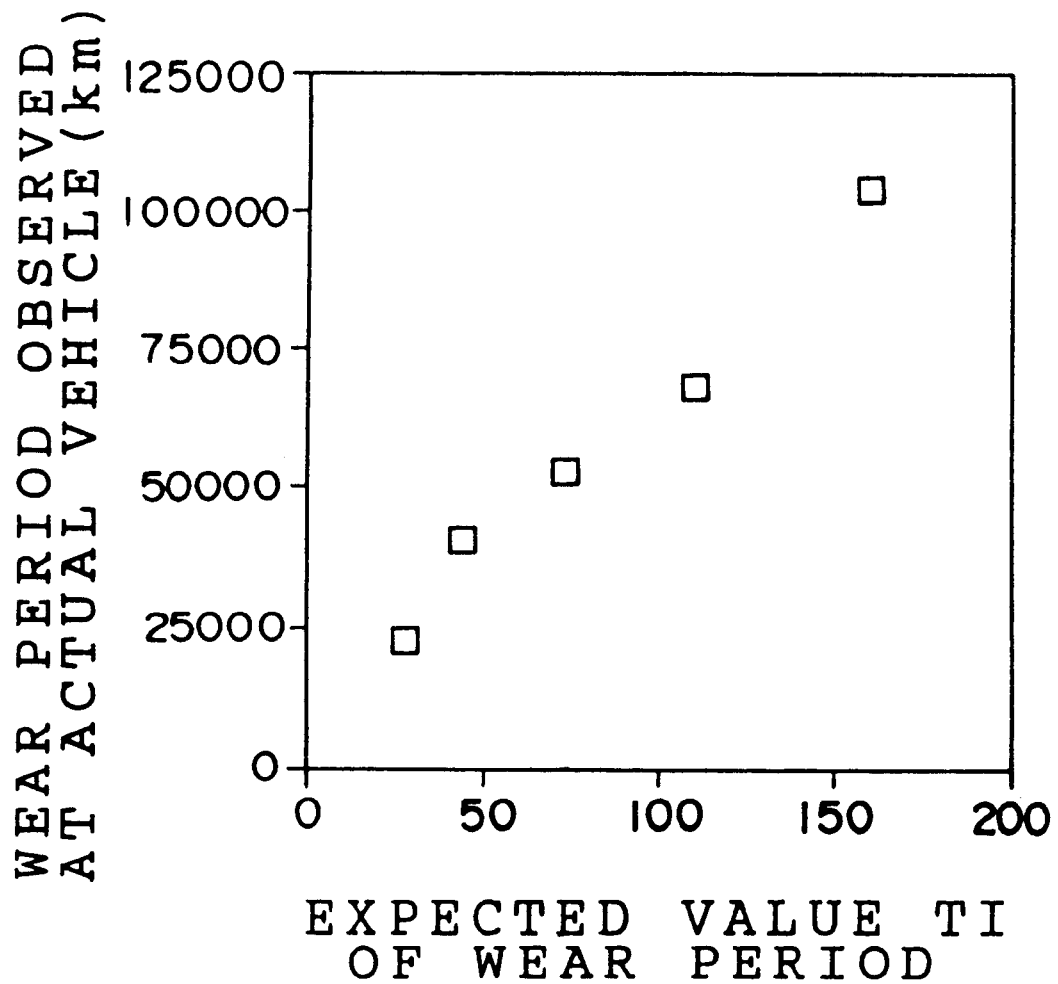

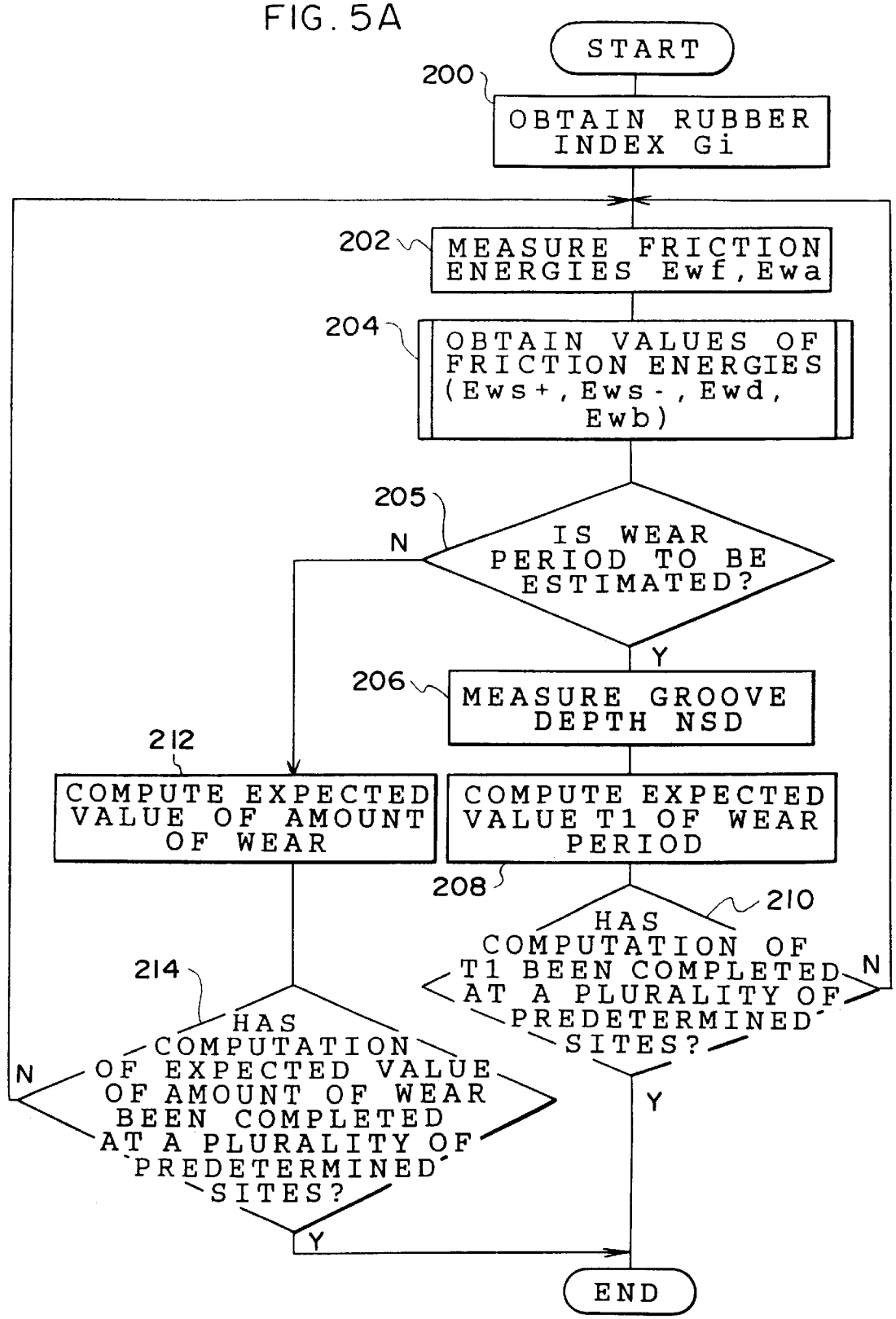

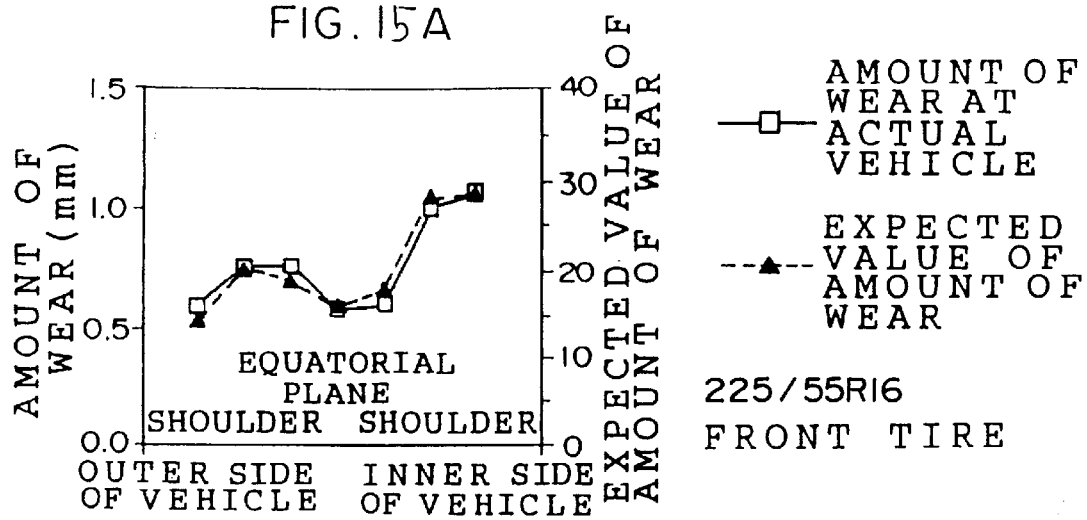
FIG. 15A  225/55R16 FRONT TIRE
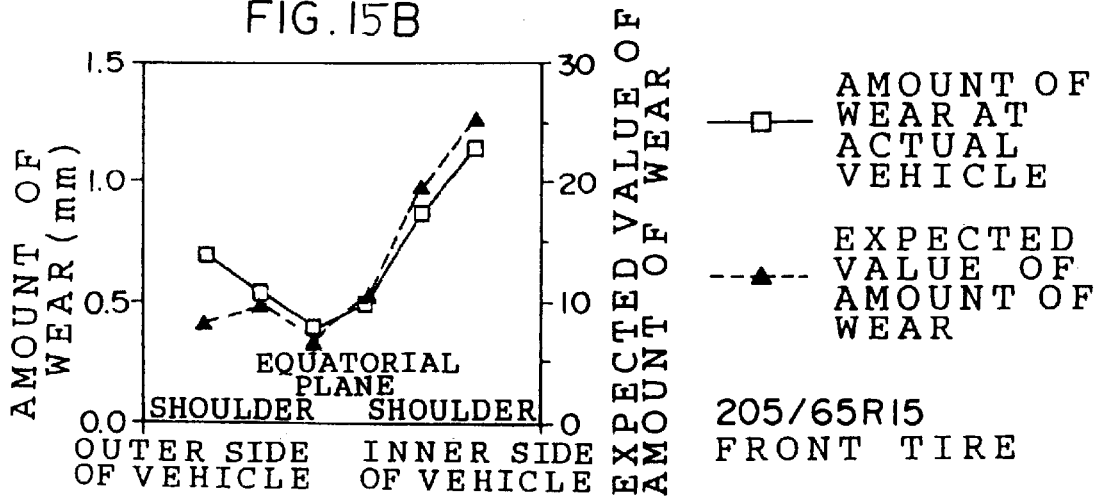
FIG. 15B  205/65R15 FRONT TIRE
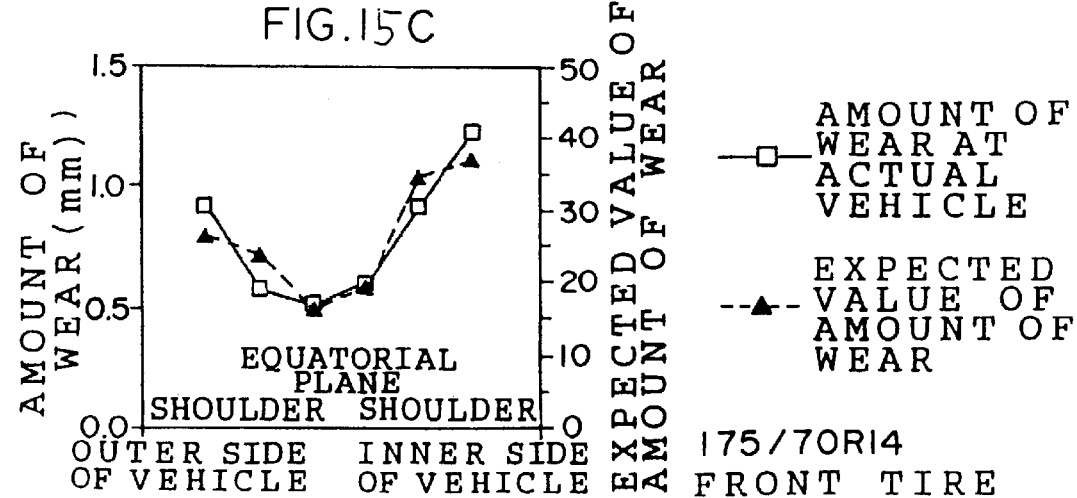
FIG. 15C  175/70R14 FRONT TIRE

METHOD FOR ESTIMATING A TIRE WEAR LIFE

BACKGROUND OF THE INVENTION

1. Field of the Invention

The present invention relates to a method for estimating a tire wear life, and more particularly, to a method for estimating a tire wear life which enables estimating the tire wear lie or the degree of wear of rubber in actual use.

2. Description of the Related Art

Heretofore, the wear life of a tire used for vehicles has been estimated from the condition of wear (the degree of wear or the amount of wear) after a vehicle mounting the tire whose wear life is to be estimated is actually driven for a specific distance (as for the definition of the word "wear life", refer to page 13 of the specification).

However, this method has a drawback in that the test is quite time-consuming because the distance to be driven by the vehicle for the test must be great in order to get an accurate measurement of the amount of wear of the tire required for a highly precise estimation.

To overcome the above drawback, in the technology disclosed in Japanese Patent Application Publication (hereinafter, referred to as JP-B) 1-56374, at least two pairs of test tires are mounted to a vehicle used for the test and are driven on roads in a manner such that the rotation speeds of the two tires are different between the pairs by a desired extent so that the wear of the tire due to the driving force and due to the braking force can be evaluated simultaneously.

As the formula for estimating the amount of wear of a tire, Schallamach's formula of the amount of wear is known. In accordance with this theoretical formula, the amount of wear M of a tire per unit distance of driving is considered to be proportional to the friction energy and can be expressed by the following formula (1):

$$M = \gamma \rho F^2 / C \qquad (1)$$

In formula (1), $\gamma$ represents the degree of wear of a tire, $\rho$ represents resilience, F represents an external force applied to the tire and C represents the rigidity of the tire against a force in the longitudinal direction or the transverse direction thereof When the rigidity C is expressed move specifically by the rigidity in the longitudinal direction, (in the driving direction) Cd, and the rigidity in the direction of braking Cb, and the rigidity in the transverse direction Cs, Schallamach's formula of the amount of wear is expressed by the following formula (2):

$$M = \gamma \rho F^2 / (Cd + Cb + Cs)$$

$$= \gamma \rho (Fx+^2/Cd + Fx-^2/Cb + Fy^2/Cs) \qquad (2)$$

In the above formula, Fx+ represents a force in the forward direction generated by a driving force, Fx− represents a force in the backwards direction generated by a braking force and Fy represents an input force in the transverse direction.

However, the technology described in the specification of JP-B 1-56374 has a drawback in that at least one actual road test must be conducted for a long time and thus it still takes a long time to estimate the tire wear life, although the time required for the test can be decreased in comparison with the time required for methods of estimation using only one pair of tires in one run of the road test.

Moreover, Schallamach's formula of the amount of wear has a drawback in that, although the formula takes rigidities in the direction of driving, in the direction of braking and in the transverse direction into consideration, accurate estimation of tire wear life of a tire mounted to a vehicle in actual use is still difficult when factors taken into consideration are limited to these parameters.

When driving a vehicle in actual use, there are more diverse factors affecting the wear of a tire such as the properties of the rubber of the tire tread portion, tire tread patterns and structures, and input forces experienced by a tire in the actual use of the tire by the customers (during driving in the conditions of actual road use of the vehicle). Therefore, in the actual driving condition of a vehicle which is affected by so many diverse factors, it is obviously difficult to accurately estimate the wear of a tire using Schallamach's formula of the amount of wear in which only rigidities in the direction of driving, in the direction of braking and in the transverse direction are considered.

SUMMARY OF THE INVENTION

The present invention has been made to overcome the above problems and has an objective of providing a method for estimating the tire wear life which enables accurate estimation of the tire wear life in a short time.

To achieve the above object, in the first aspect of the method for estimating the tire wear life of the present invention, a friction energy of the tire Ewf in free rolling, a friction energy of the tire Ewa when the tire is mounted with a toe angle, a friction energy of the tire Ews under application of a side force to the tire, a friction energy of the tire Ewd under application of a driving force to the tire and a friction energy of the tire Ewb under application of a braking force to the tire are obtained. In addition, a friction energy ew of a rubber sample made of the same material as the material used in the tire tread portion under a severity substantially the same as the severity in the actual use of the tire and a wear depth W per given driving distance are also obtained.

The tire wear life is estimated on the basis of a value including a product of a rubber index Gi and a reciprocal of a friction energy Ew (1/Ew), i.e., Gi/Ew. The rubber index Gi is a value obtained by dividing the friction energy ew by the wear depth W, i.e., ew/W. The friction energy Ew is expressed by the following formula:

$$Ew = Ewf + Ewa + Ews + Ewb + Ewd$$

In accordance with the first aspect of the present invention, the friction energy of the tire Ewf in free rolling and the friction energy of the tire Ewa when the tire is mounted with a toe angle are used as the factors for estimating the tire wear life in addition to the friction energy of the tire Ews under application of a side force (force in the transverse direction) to the tire, the friction energy of the tire Ewd under application of a driving force to the tire and the friction energy of the tire Ewb under application of a braking force to the tire. Therefore, the tire wear life can be estimated more accurately in comparison with the estimation of the tire wear life in accordance with the Schallamach's formula of the amount of wear in which rigidity in the direction of driving, in the direction of braking and in the transverse direction alone are taken into consideration.

In this aspect, the rubber index Gi is measured under a severity which is approximately the same as the severity in the actual use of the tire and used for estimation of the tire wear life. Therefore, the tire wear life can be estimated more accurately in comparison with the estimation using the friction resistance index obtained by the conventional Lambourn abrasion tester specified in Japanese Industrial Standard K 6264.

In the second aspect of the present invention, it is preferable that the value including the product Gi/Ew is a value selected from the product Gi/Ew or a value obtained by multiplying the product Gi/Ew by a remaining groove depth remaining before the groove depth reaches the limit for disposal of the tire.

As the remaining groove depth remaining before the groove depth reaches the limit for disposal of the tire, it is preferable that a value obtained by subtracting the value which is considered to be the limit for disposal of the tire, for example 1.6 (mm), from the groove depth NSD is used.

In the third aspect of the present invention, using an input force in a transverse direction Fy, a force in a forward direction Fx+ generated by the driving force, a force in a backward direction Fx− generated by the braking force, undetermined coefficients S, D and B and exponents ns, nd and nb, the friction energy Ews, the friction energy Ewd and the friction energy Ewb are expressed by the following formulae:

$$Ews = S \times Fy^{ns}$$

$$Ewd = D \times Fx+^{nd}$$

$$Ewb = B \times FX-^{nb}$$

The undetermined coefficients S, D and B and the exponents ns, nd and nb are obtained in advance on the basis of values of the friction energy Ews, the friction energy Ewd and the friction energy Ewb measured under application of a given value of the input force in the transverse direction Fy, a given value of the force in the forward direction Fx+ and a given value of the force in the backward direction Fx−, respectively. Values of the input force in the transverse direction Fy, the force in the forward direction Fx+ and the force in the backward direction Fx− are determined on the basis of RMS values of the distribution of acceleration in the transverse direction at the center of gravity position of the vehicle and the distribution of acceleration in the longitudinal direction at the center of gravity position of the vehicle in the actual use of the vehicle. The friction energy Ews, the friction energy Ewd and the friction energy Ewb are obtained on the basis of the determined values of the input force in the transverse direction Fy, the force in forward direction Fx+ and the force in the backward direction Fx− in accordance with the above formulae.

In accordance with the third aspect of the present invention, the estimation reflects input forces in the actual use of the tire because the friction energy Ews, the friction energy Ewd and the friction energy Ewb are obtained on the basis of RMS values of the distribution of acceleration in the transverse direction at the center of gravity position of the vehicle or the distribution of acceleration in the longitudinal direction at the center of gravity position of the vehicle in the actual use of the tire. Therefore, the tire wear life can be estimated more accurately in comparison with estimations which do not reflect input forces in the actual use of the tire.

In the fourth aspect of the present invention, the exponents ns, nd and nb which are obtained on the basis of measured values in the third aspect are each set at a fixed value in the range of 1.5 to 3 and preferably in the range of 2 to 3. The undetermined coefficients S, D and B are obtained in advance on the basis of values of the friction energy Ews, the friction energy Ewd and the friction energy Ewb measured under application of a given value of the input force in the transverse direction Fy, a given value of the force in the forward direction Fx+ and a given value of the force in the backward direction Fx−, respectively.

In accordance with the fourth aspect, the exponents ns, nd and nb are set at fixed values in the range of 1.5 to 3. Therefore, the undetermined coefficients S, D and B can be obtained more easily in comparison with the case in which the exponents ns, nd and nb are not set at fixed values.

In the fifth aspect of the present invention, the friction energy Ews is divided into a friction energy Ews+ generated in the rightward turn of the vehicle to which the tire is mounted and a friction energy Ews− generated in the leftward turn of the vehicle to which the tire is mounted and each of Ews+ and Ews− is obtained on the basis of the Ackerman characteristic and the toe angle of the vehicle. The friction energy Ews is obtained as the sum of the friction energy Ews+ and the friction energy Ews−, i.e., Ews++ Ews−.

In accordance with the fifth aspect, the friction energy Ews can be obtained in conditions closer to those of actual use of the tire in comparison with the case in which the friction energy Ews is obtained without taking the Ackerman characteristic and the toe angle into consideration.

In the sixth aspect of the present invention, using an input force in the transverse direction Fy+ generated in the rightward turn of the vehicle, an input force in a transverse direction Fy− generated in the leftward turn of the vehicle, a force in the forward direction Fx+ generated by the driving force, a force in the backward direction Fx− generated by the braking force, undetermined coefficients S1, S2, D and B and exponents ns1, ns2, nd and nb, the friction energy Ews+, the friction energy Ews−, the friction energy Ewd and the friction energy Ewb are expressed by the following formulae:

$$Ews+ = S1 \times Fy+^{ns1}$$

$$Ews- = S2 \times Fy-^{ns2}$$

$$Ewd = D \times Fx+^{nd}$$

$$Ewb = B \times FX-^{nb}$$

The undetermined coefficients S1, S2, D and B and the exponents ns1, ns2, nd and nb are obtained in advance on the basis of values of the friction energy Ews+, the friction energy Ews−, the friction energy Ewd and the friction energy Ewb measured under application of a given value of the input force in the transverse direction Fy+, a given value of the input force in the transverse direction Fy−, a given value of the force in the forward direction Fx+ and a given value of the force in the backward direction Fx−, respectively.

Values of the input force in the transverse direction Fy+, the input force in the transverse direction Fy−, the force in the forward direction Fx+ and the force in the backward direction Fx− are determined on the basis of RMS values of the distribution of acceleration in the transverse direction at the center of gravity position of the vehicle or the distribution of acceleration in the longitudinal direction at the center of gravity position of the vehicle in the actual use of the vehicle. The friction energy Ews+, the friction energy Ews−, the friction energy Ewd and the friction energy Ewb are obtained on the basis of the determined values of the input force in the transverse direction Fy+, the input force in the transverse direction Fy−, the force in forward direction Fx+ and the force in the backward direction Fx− in accordance with the above formulae in which the coefficients and the exponents have been determined.

In accordance with the sixth aspect of the present invention, the friction energy Ews+, the friction energy Ews−, the friction energy Ewd and the friction energy Ewb are obtained on the basis of RMS values of the distribution of acceleration in the transverse direction at the center of gravity position of the vehicle or the distribution of acceleration in the longitudinal direction at the center of gravity position of the vehicle in the actual use of the vehicle. As the friction energies are obtained in conditions closer to those of the actual use of the tire, the tire wear life can be estimated more accurately in comparison with the case in which the input forces in the actual use of the tire are not taken into consideration.

In the seventh aspect of the present invention, the exponents ns1, ns2, nd and nb which are obtained on the basis of measured values in the sixth aspect are each set at a fixed value in the range of 1.5 to 3 and preferably in the range of 2 to 3. The undetermined coefficients S1, S2, D and B are obtained in advance on the basis of values of the friction energy Ews, the friction energy Ewd and the friction energy Ewb measured under application of a given value of the input force in the transverse direction Fy+, a given value of the input force in the transverse direction Fy−, a given value of the force in the forward direction Fx+ and a given value of the force in the backward direction Fx−, respectively.

In accordance with the seventh aspect, the exponents ns1, ns2, nd and nb are set at fixed values in the range of 1.5 to 3. Therefore, the undetermined coefficients S1, S2, D and B can be obtained more easily in comparison with the case in which the exponents ns1, ns2, nd and nb are not set at fixed values.

In the eighth aspect of the present invention, the tire wear life is estimated at a plurality of portions of the tire.

In the ninth aspect of the present invention, it is preferable that the friction energy Ew is expressed as a friction energy value per unit area and unit distance of driving standardized by using a rolling radius of the tire. When the friction energy Ew is expressed as described above, results of estimation of the tire wear life with a plurality of tires having different tire sizes can be compared with each other.

In the tenth aspect of the present invention, on the basis of a measured value of the rubber index Gi and the friction energies Ewf, Ewa, Ews+, Ews−, Ewd, and Ewb, an expected value of the amount of wear is expressed by a formula:

$$Wt=Ew/Gi$$

$$=\{(Ewf)+(Ewa)+(Ews+)+(Ews-)+(Ewd)+(Ewb)\}/Gi$$

BRIEF DESCRIPTION OF THE DRAWINGS

FIG. 4A shows a graph exhibiting the relation between the expected value of the tire wear life obtained in accordance with formula (9) based on the first embodiment and the tire wear life obtained by an actual vehicle test.

FIG. 5A shows a schematic flow chart exhibiting the procedures for estimation of the tire wear life in the first embodiment.

FIG. 15A shows a graph exhibiting the relation between the expected value of the tire wear life and the amount of wear of a tire attached to an actual vehicle in the transverse direction of the tread. (A case in which a tire of a size 225/55R16 was used as a front tire) according to the third embodiment.

FIG. 15B shows a graph exhibiting the relation between the expected value of the tire wear life and the amount of wear of a tire attached to an actual vehicle in the transverse direction of the tread. (A case in which a tire of a size 205/65R15 was used as a front tire) according to the third embodiment.

FIG. 15C shows a graph exhibiting the relation between the expected value of the tire wear life and the amount of wear of a tire attached to an actual vehicle in the transverse direction of the tread. (A case in which a tire of a size 175/70R14 was used as a front tire) according to the third embodiment.

DETAILED DESCRIPTION OF THE EMBODIMENTS

Figure 1:
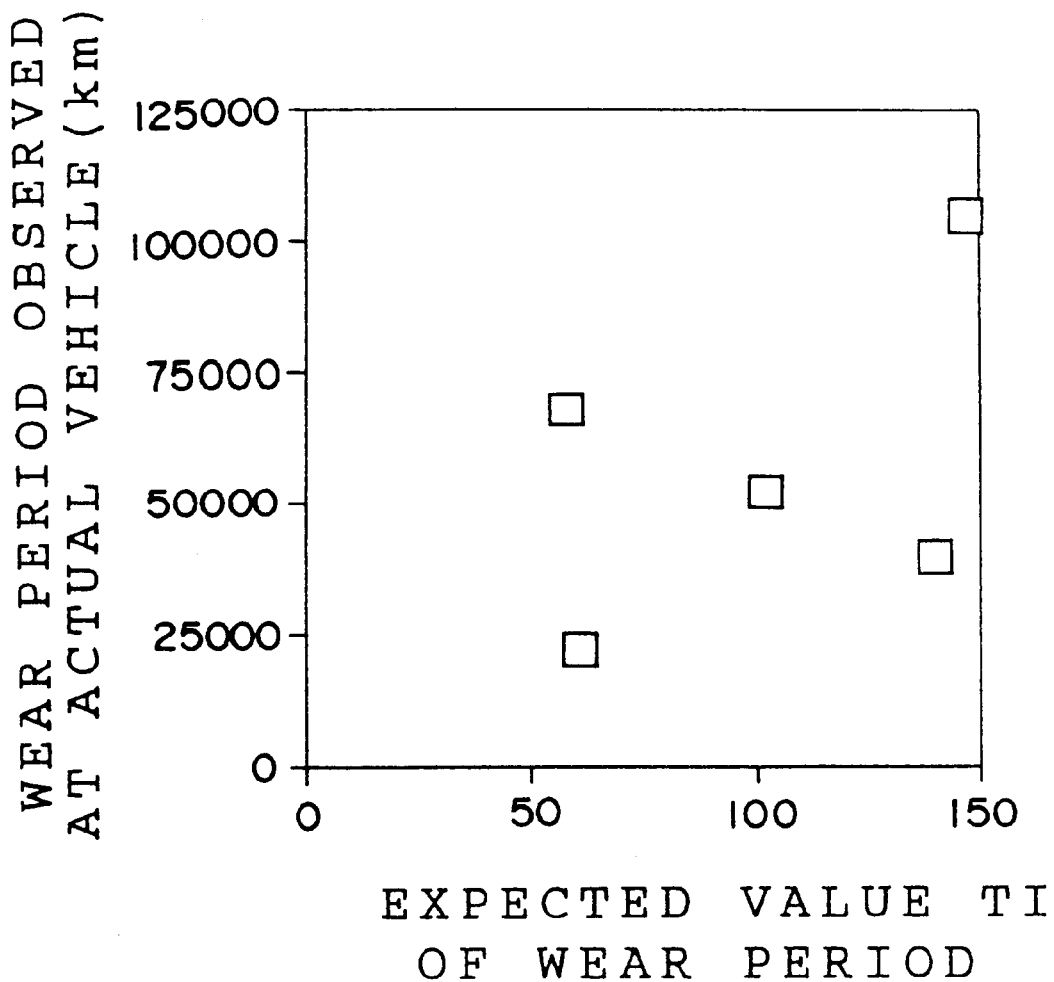
FIG. 1 shows a graph exhibiting the relation between the expected value of the tire wear life obtained in accordance with formula (5) in an embodiment described below and the tire wear life actually observed at an actual vehicle test.

The embodiments of the present invention will now be described with reference to the drawings.

The general method for estimating the tire wear life used in the embodiments of the present invention will be systematically described.

In the embodiments of the present invention, the term "wear life" refers to the period of time from the time the tire is new to the time the tire is worn to the extent that the properties exhibited thereby deteriorate from excellent or good to satisfactory. More concretely, "wear life" refers to the period of time from the time the tire is new to the time the groove depth of the read has shrunk to, for example, 1.6 mm.

In the present method for estimating the tire wear life, the friction energy Ewf of a tire in free rolling and the friction energy of the tire in a state in which a toe angle is imparted to the tire are obtained.

The friction energy Ews under application of a side force to the tire, the friction energy Ewd under application of a driving force to the tire and the friction energy Ewb under application of a braking force to the tire are also obtained when a camber angle, a toe angle and an applied load are set with consideration of dynamic variations which occur in the tire during the use of the tire.

The friction energy ew of a rubber sample made of the same material as the material used in the tire tread portion is obtained under a severity which is approximately the same as the severity in the actual use of the tire, and a wear depth W per given driving distance is also obtained. Then, the tire wear life is estimated on the basis of a value including the product of a rubber index Gi and the reciprocal of a friction energy Ew (1/Ew), i.e., Gi/Ew. The rubber index Gi is obtained by dividing the friction energy ew by the wear depth W, i.e., ew/W. The friction energy is expressed by the following formula:

$$Ew=Ewf+Ewa+Ews+Ewb+Ewd$$

The principle according to which the above values and combinations of the values can work as parameters for estimating the tire wear life in the present invention will be described in the following.

It is assumed that wear of a tire is caused by two major contributing factors: one factor G being the rubber material itself of the tire tread portion and the other factor E being the tread pattern and the structure of the tire.

A wear resistance index G1 (%) of rubber of the tire tread portion is measured by the Lambourn abrasion test and used as the factor G related to the rubber material of the tire tread portion. A friction energy Ew (kgf/cm$^2$, N/m$^2$ in accordance with the SI unit system) which is a value per unit area and unit distance of driving standardized by using a rolling radius of the tire is measured and used as the factor E related to the tread pattern and the structure of the tire. The Lambourn abrasion test is specified in Japanese Industrial Standard K 6264 which is one of the methods for measuring wear (resistance) of a vulcanized rubber or an elastic material and uses the Lambourn abrasion tester for the measurement. The wear resistance index G1 can be obtained in accordance with this method.

It is reported in Paper No. 79 of the 131st Meeting of the American Chemical Society in 1987 and elsewhere that the wear resistance index G1 obtained in accordance with the Lambourn abrasion test is effective as the index showing the wear property of top rubber (the surface of the rubber) in a tire.

It is reported in "A Trial on Laboratory Evaluation of Tire Wear" by YOKOHAMA RUBBER Co., Ltd. in the preprint for the fall lecture meeting of the Japanese Automotive Engineers Society in 1982 and elsewhere that the friction energy Ew is an effective physical factor to evaluate contribution of a tread pattern and a structure to tire wear.

Therefore, the present inventors made studies on estimating the wear resistance property of a tire by using the wear resistance index G1 and the friction energy Ew of rubber.

It is considered that the greater the wear resistance index G1, the longer the tire wear life and that the greater the friction energy Ew, the shorter the tire wear life. Therefore, a wear resistance coefficient m is defined by the following formula (3):

$$m=G1/Ew \qquad (3)$$

It is considered that the deeper the remaining groove depth of the tire, the longer the tire wear life. Therefore, on the basis of the wear resistance coefficient m, an expected value of a tire wear life T1 is defined by the following formula (4):

$$T1=m\times(NSD-1.6)$$
$$=(G1/Ew)\times(NSD-1.6) \qquad (4)$$

In the above formula, NSD represents a groove depth (mm) of the tire and 1.6 corresponds to the groove depth of 1.6 (mm) which is considered to be the limit groove depth at which the tire should be disposed.

Similarly to Schallamach's formula, the friction energy Ew is considered to be expressed by the sum of the friction energy of the tire Ews when a side force (a force in the transverse direction) is applied to the tire, the friction energy of the tire Ewd under application of a driving force to the tire and the friction energy of the tire Ewb under application of a braking force to the tire. Formula (4) is then modified to the following formula (5):

$$T1=\{G1/(Ews+Ewd+Ewb)\}\times(NSD-1.6) \qquad (5)$$

In accordance with formula (5), five expected values of the wear life of tires T1 were calculated under application of 5 types of input forces generally found in the actual use of the tire. The actual wear life of the tire was also measured under the corresponding conditions by the actual vehicle test.

FIG. 1 shows a graph exhibiting the relation between the expected value T1 of the tire wear life and the actual tire wear life measured in an actual vehicle test. As shown in FIG. 1, the expected value T1 of the tire wear life T1 and the tire wear life obtained in the actual vehicle test showed a poor correlation. Therefore, it is confirmed that the accuracy of estimation of the tire wear life would not be improved any nore as long as using the expected value of the tire wear life described above is used.

Figure 2:
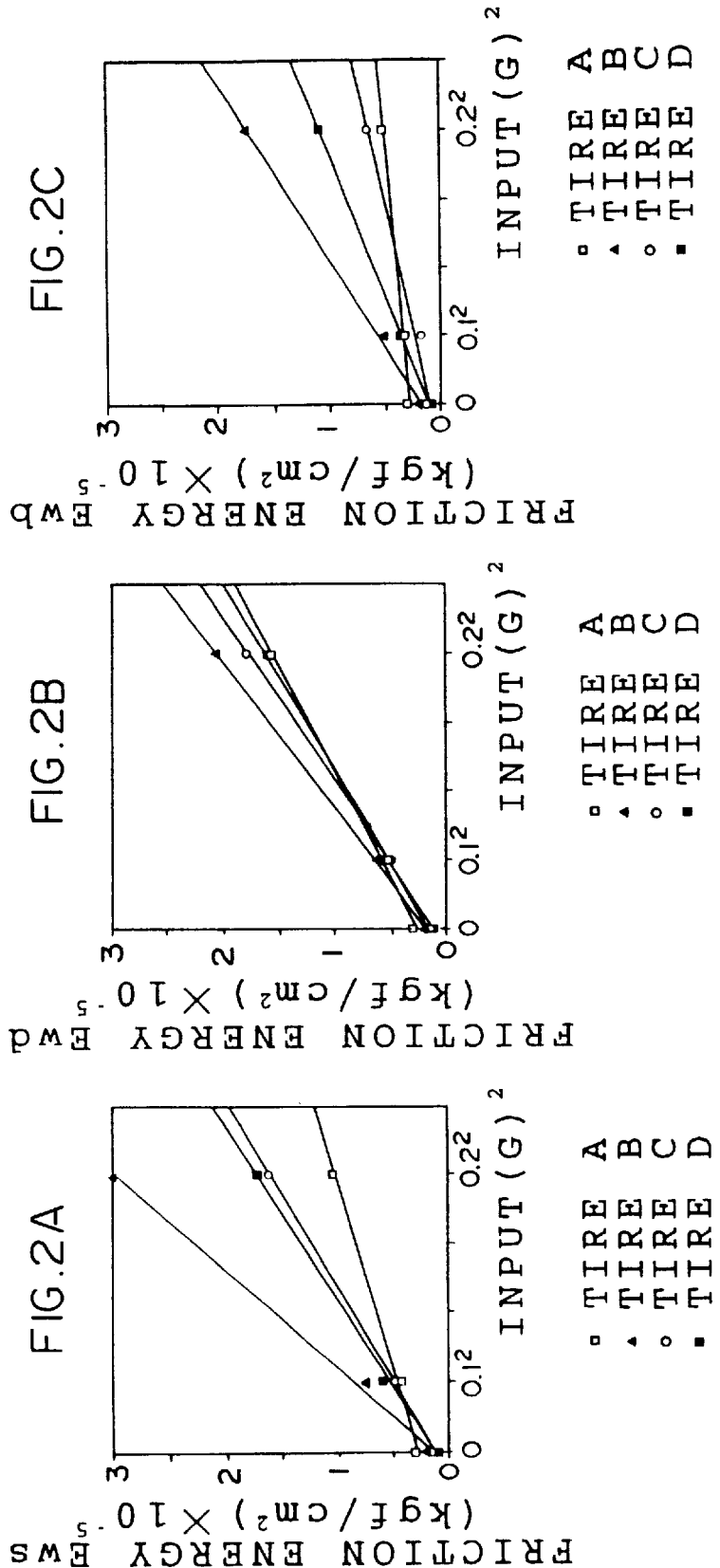
FIG. 2A shows a graph exhibiting the relation between the square of an input force and the friction energy Ews of a tire under application of a side force.
FIG. 2B shows a graph exhibiting the relation between a square of an input force and the friction energy Ewd of a tire under application of a driving force.
FIG. 2C shows a graph exhibiting the relation between the square of an input force and the friction energy Ewb of a tire under application of a braking force.

The friction energies were studied in detail to elucidate the cause of the poor correlation obtained above. As a result, it was found that, with four types of tires A to D, the friction energies Ews, Ewd and Ewb were proportional to the square of the respective input forces as shown in FIGS. 2A to 2C. This result agrees with Schallamach's formula. However, lines in the graphs did not pass through the origin and gave respective positive intercepts.

The positive intercepts were studied in detail and, as a result, it was found that the friction energy of the tire Ewf in free rolling (when the tire is allowed to roll freely) and the friction energy of the tire Ewa when a toe angle is imparted to the tire are major factors contributing to the friction energy corresponding to the above positive intercept.

On the basis of the above findings, the friction energy Ew is calculated in accordance with the following formula (6):

$$Ew = Ewf + Ewa + Ews + Ewb + Ewd \quad (6)$$

and the expected value T1 of the tire wear life of a tire is calculated in accordance with the following formula (7):

$$T1 = (G1/Ew) \times (NSD - 1.6) \quad (7)$$

Figure 3:
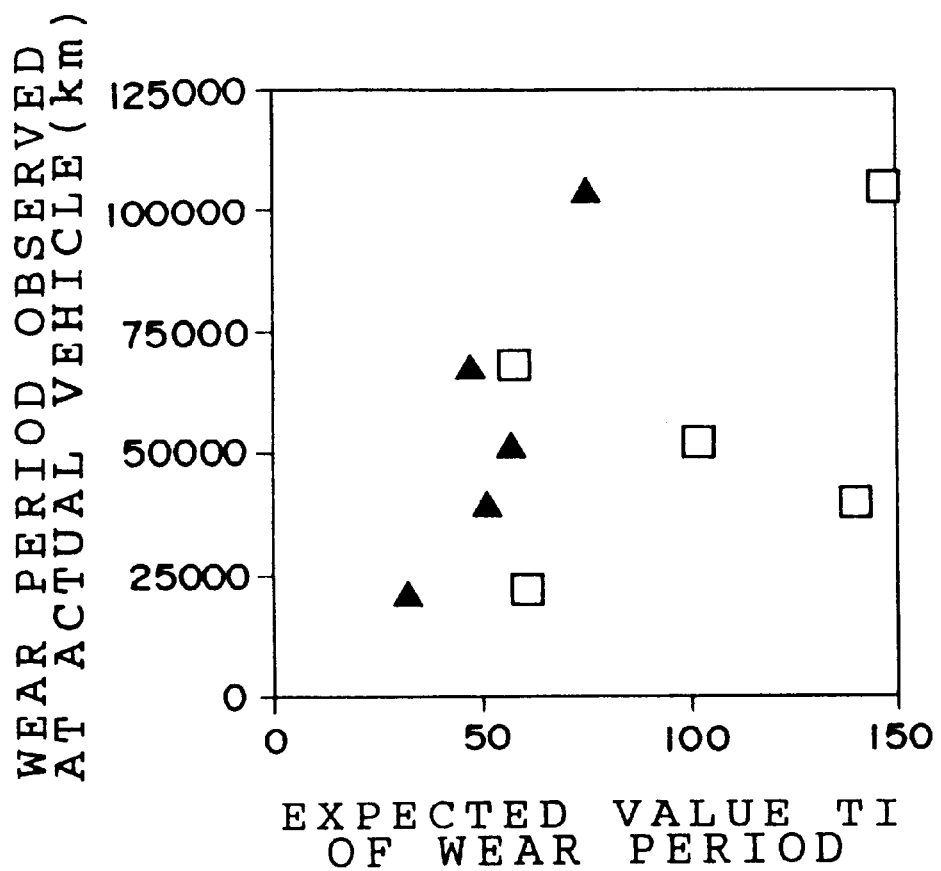
FIG. 3 shows a graph exhibiting the relation between the expected value of the tire wear life obtained in accordance with formula (7) and the tire wear life obtained by an actual vehicle test.

In accordance with formula (7), expected values T1 of the tire wear life of tires were calculated under the application of five types of input forces in the same manner as that conducted in studying formula (5). As a result, it was found that the correlation between the expected value Ti of the tire wear life and the tire wear life measured by the actual vehicle test was improved as shown in FIG. 3. Thus, it was found that the accuracy of estimation of tire wear life obtained on the basis of the expected value of the tire wear life T1 described above would be significantly improved.

The improvement in the correlation between the expected tire wear life T1 and the tire wear life obtained by the actual use of a vehicle shown in FIG. 3 is still not satisfactory. As a result of studies on the cause of the unsatisfactory correlation, it was found that the worn surface (the condition of the surface after wear) of the rubber test piece in the Lambourn abrasion test and the worn surface of the tire tread portion in the tire attached to the vehicle for the road test were markedly different, and the possibility that this difference was the cause of the unsatisfactory correlation was great.

This difference arises from a markedly greater severity in the Lambourn abrasion test than the severity of the tire in actual use. Severity here shows the degree of severity of friction. The greater the severity, the greater the slip ratio and the friction energy.

In more detail, the slip ratio in the Lambourn abrasion test specified in Japanese Industrial Standard K 6264 can normally be adjusted in the range of 5 to 80%. When the slip ratio is the minimum value of the range, i.e., 5%, the friction energy per unit area and unit distance of driving is in the range of $100 \times 10^{-5}$ to $300 \times 10^{-5}$ (kgf/cm$^2$). On the other hand, the friction energy per unit area and unit distance of driving in actual use is in the range of $10 \times 10^{-5}$ to $40 \times 10^{-5}$ (kgf/cm$^2$). These two values of the friction energies in respective ranges are different from each other to a significant degree.

Therefore, a tester which allows the wear test of a rubber test piece under the same degree of severity as the severity in actual use (a slip ratio of about 0.5 to 5%) was used and the friction energy ew (kgf/cm$^2$) per unit area and unit distance of driving and the wear depth (in this case, the wear depth of the rubber test piece corresponding to the wear depth in actual use after driving for 1000 km (mm/1000 km)) under the severity corresponding to the severity in the actual use were measured. As the parameter which was used in place of the above friction coefficient G1, a rubber index Gi was defined by the following formula (8):

$$Gi = ew/W \quad (8)$$

Using the above rubber index Gi, the expected value of the tire wear life T1 was calculated in accordance with the following formula (9):

$$T1 = (Gi/Ew) \times (NSD - 1.6) \quad (9)$$

The expected value of the tire wear life T1 was obtained by using formula (9) under application of 5 types of input forces in the same manner as that in the study using formula (5). As shown in FIG. 4A, it was found that the correlation between the expected value T1 of the tire wear life and the tire wear life obtained by the actual use of a vehicle was remarkably improved in comparison with the correlation between the expected value T1 of the tire wear life obtained in accordance with formula (7) and the tire wear life obtained by the actual use of a vehicle shown in FIG. 3. Thus, it is found that the accuracy of estimation of the tire wear life would be significantly improved when the expected value of the tire wear life is estimated in accordance with formula (9) (The first embodiment).

It should be noted that, in the actual use of a tire attached to a vehicle, alignments and loads applied to the tire change depending on the posture of the vehicle. Therefore, it is preferable that factors related to dynamic changes in alignments and loads movement in the actual use of the vehicle are reflected in the friction energies Ews, Ewd and Ewb. For this purpose, a camber angle, a toe angle and a load in which dynamic changes in the actual use of the tire are taken into consideration are added as factors to the tire when the friction energies Ews, Ewd and Ewb are obtained (the third embodiment).

Figure 4B:
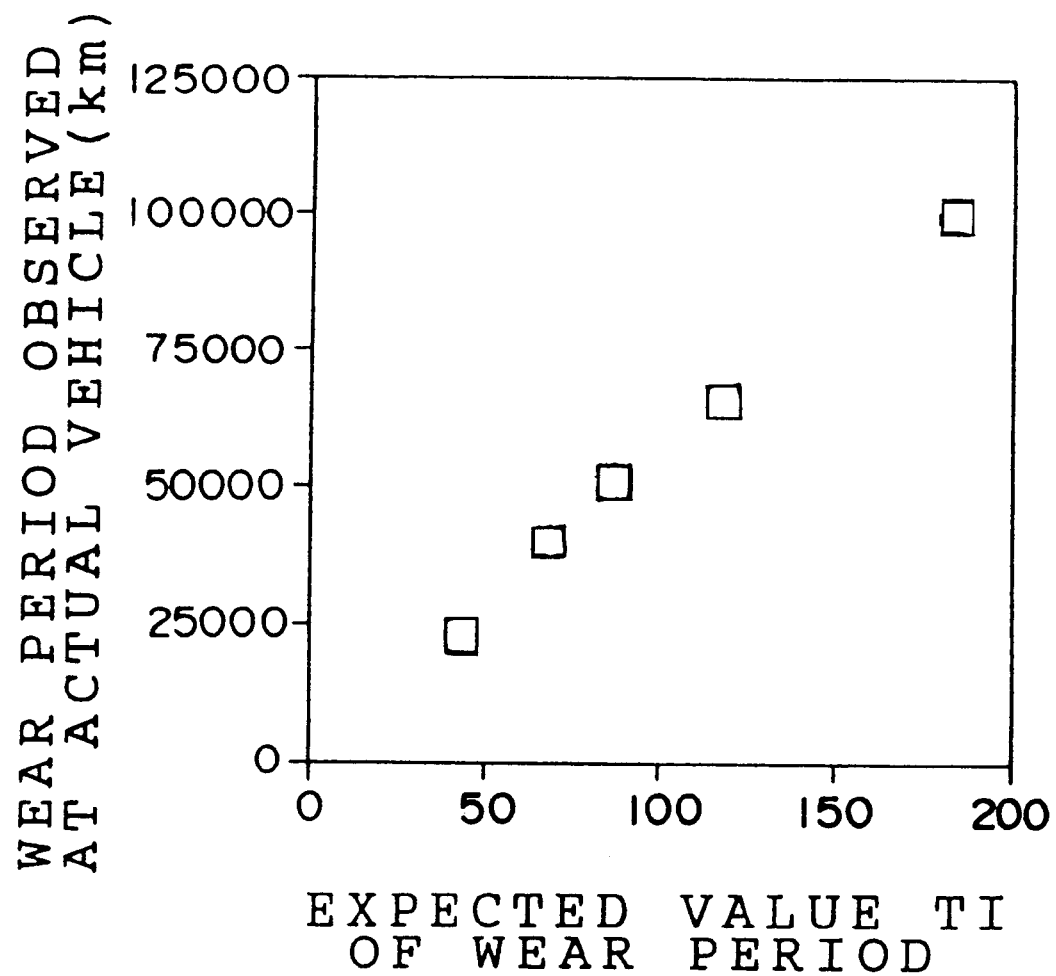
FIG. 4B shows a graph exhibiting the relation between the expected value of the tire wear life obtained in accordance with formula (9) based on the third embodiment and the tire wear life obtained by an actual vehicle test.

The expected value of the tire wear life T1 was obtained, in a way similar to the first embodiment, by using formula (9) under application of 5 types of input forces in the same manner as that in the study using formula (5). As shown in FIG. 4B, it was found that the correlation between the expected value T1 of the tire wear life and the tire wear life obtained by the actual use of a vehicle was remarkably improved in comparison with the correlation between the expected value T1 of the tire wear life obtained in accordance with formula (7) and the tire wear life obtained by the actual use of a vehicle shown in FIG. 3. It should be noted that the results (the degree of correlation) obtained in the third embodiment is more excellent than that obtained in the first embodiment, To obtain the camber angle, the toe angle and the load in which dynamic changes in the actual use of the tire are taken into consideration, a vehicle model having 5 or more degrees of freedom including degrees of freedom in the longitudinal direction, in the transverse direction, yawing, for rolling and pitching as factors related to the dynamic change in the alignment of the vehicle in the actual use is used. The degree of freedom in the vertical direction may also be included where necessary (the number of degrees of freedom is 6 in this case). The friction energies are obtained by using the above vehicle model as follows.

To obtain the camber angle, the toe angle and the load for obtaining the friction energy Ews, a vehicle making a turn is used as a model and the speed and the centrifugal acceleration (acceleration in the direction of the center of the locus circle of the turn) of the vehicle are set at suitable values. The camber angle, the toe angle and the load of a tire attached to the vehicle which is driven along a predetermined circular course with a given radius are calculated by computer simulation using the above model.

Although the input forces described above are likely to be found in various (each different) states in the actual use of a vehicle, the input forces can still be represented by the input forces in the above-mentioned circular turning state, by using the representative speed and the representative acceleration of the vehicle as the speed and the centrifugal acceleration in the above driving along the circular course with the steady speed, respectively. It is preferable that the average speed in the driving mode in the simulation is used as the above representative speed of the vehicle and the RMS value of the acceleration in the driving mode in the simulation is used as the above representative acceleration.

To obtain the camber angle, the toe angle and the load for obtaining the friction energy Ewd, the acceleration by driving of a vehicle is set at a suitable value and camber angle, the toe angle and the load of the tire attached to the vehicle are obtained by computer simulation using the above model.

Although the input forces described above are likely to be found in various (each different) states in the actual use of a vehicle, the input forces can still be represented by the input forces in the constant-inertia state, by using the representative driving acceleration of the vehicle as the acceleration of the above vehicle by driving. Actually, the RMS value of the acceleration in the driving mode in the simulation is used as the above representative acceleration.

Similarly, to obtain the camber angle, the toe angle and the load for obtaining the friction energy Ewb, the acceleration by braking of a vehicle is set at a suitable value and the camber angle, the tow angle and the load of the tire attached to the vehicle are obtained by computer simulation using the above model.

Although the input forces described above are likely to be found in various (each different) states in the actual use of a vehicle, the input forces can still be represented by the input forces in the constant-inertia state, by using the representative braking acceleration of the vehicle as the acceleration of the above vehicle by braking. Actually, the RMS value of the acceleration in the driving mode in the simulation is used as the above representative acceleration.

On the basis of the above principle, in the method for estimating the tire wear life of the present invention, the above friction energies Ewf, Ewa, Ews, Ewd and Ewb are obtained and the friction energy ew and the wear depth W per given distance of driving of a rubber sample made of the same material as the material used in the tire tread portion are also obtained under approximately the same severity as the severity in the actual use of the tire.

The toe angle is the angle between the direction of driving and the equatorial plane of the tire. The side force is the force in the direction orthogonal to the rolling direction of the tire. The driving force is the force in the moving direction of the tire generated by driving the tire. The bracing force is the force generated by braking in the direction opposite to the driving force.

When the friction energy Ewf of the tire in free rolling is obtained, it is preferable that the initial camber angle of the vehicle to which the tire is attached is employed.

The tire wear life can be estimated on the basis of a value including the product of the rubber index Gi and the reciprocal of the friction energy Ew expressed by formula (6) 1/Ew, i.e., Gi/Ew. The rubber index Gi is the value obtained by dividing the friction energy ew by the wear depth W: ew/W.

As described above, in accordance with the method of the present invention, the friction energies Ewf, Ewa, Ews, Ewd and Ewb are used as the factors to estimate the tire wear life. Therefore, the tire wear life can be estimated more accurately in comparison with the estimation of the tire wear life in accordance with Schallamach's formula in which rigidities in the direction of driving, in the direction of braking and in the transverse direction alone are taken into consideration.

Moreover, the rubber index Gi under the severity which is approximately the same as the severity in actual use is measured and used for the estimation. Therefore, the tire wear life can be estimated more accurately in comparison with the estimation of the tire wear life using the wear resistance index obtained by the conventional Lambourn abrasion test specified in Japanese Industrial Standard K 6264.

In addition, when the friction energies Ews, Ewd and Ewb are obtained, the measurements are made using a camber angle, a toe angle and a load which reflect dynamic changes during the actual use of the tire. Therefore, the tire wear life can be estimated more accurately in comparison with the estimation without such a camber angle, toe angle or load.

In the method for estimating a tire wear life of the present invention, it is preferable that the value containing the product Gi/Ew is a value selected from the product Gi/Ew and a value obtained by multiplying the product Gi/Ew by a remaining groove depth which is the groove depth remaining before the groove depth reaches a limit for disposal of the tire. As the remaining groove depth remaining before the groove depth reaches a limit for disposal of the tire, it is preferable that a value obtained by subtracting the value which is considered to be the limit for disposal of the tire, for example 1.6 (mm), from the groove depth NSD is used.

The groove depth NSD of a tire may be an average value of a plurality of groove depths in the tire tread portion or the minimum value of a plurality of groove depths in the tire tread portion.

In the method for estimating a tire wear life of the present invention, using an input force in a transverse direction Fy, a force in the forward direction Fx+ generated by the driving force, a force in the backward direction Fx− generated by the braking force, undetermined coefficients S, D and B and exponents ns, nd and nb, the friction energy Ews, the friction energy Ewd and the friction energy Ewb may be expressed by the following formulae (10) to (12):

$$Ews = S \times Fy^{ns} \qquad (10)$$

$$Ewd = D \times Fx+^{nd} \qquad (11)$$

$$Ewb = B \times FX-^{nb} \qquad (12)$$

In this case, the undetermined coefficients S, D and B and the exponents ns, nd and nb are obtained in advance on the basis of values of the friction energy Ews, the friction energy Ewd and the friction energy Ewb measured under application of a given value of the input force in the transverse direction Fy, a given value of the force in the forward direction Fx+ and a given value of the force in the backward direction Fx−, respectively.

Values of the input force in the transverse direction Fy, the force in the forward direction Fx+ and the force in the backward direction Fx− are determined on the basis of RMS values of the distribution of acceleration in the transverse direction at the center of gravity position of the vehicle and the distribution of acceleration in the longitudinal direction at the center of gravity position of the vehicle in the actual use of the vehicle. The friction energy Ews, the friction energy Ewd and the friction energy Ewb are then obtained on the basis of the determined values of the input force in the transverse direction Fy, the force in the forward direction Fx+ and the force in the backward direction Fx− in accordance with the above formulae (10) to (12) in which the coefficients and the exponents have been determined.

The transverse direction, the forward direction and the backward direction are directions in relation to the direction in which the tire advances when rotated.

The RMS values of the distribution of acceleration in the transverse direction at the center of gravity position of the vehicle and the distribution of acceleration in the longitudinal direction at the center of gravity position of the vehicle during actual use of the vehicle can each be obtained as the square root of the average of the square of accelerations in a given range in each distribution of acceleration.

The friction energy Ews, the friction energy Ewd and the friction energy Ewb are values reflecting the input forces in actual use because the friction energies are obtained on the basis of the RMS values of the distribution of acceleration in the transverse direction at the center of gravity position of the vehicle and the distribution of acceleration in the longitudinal direction at the center of gravity position of the vehicle during actual use of the vehicle. Therefore, the tire wear life can be estimated more accurately in comparison with the case in which input forces in the actual use of the vehicle are not reflected.

In the method for estimating a tire wear life of the present invention, each of the above exponents ns, nd and nb may be set at a fixed value in the range of 1.5 to 3. In this case, the undetermined coefficients S, D and B are obtained in advance on the basis of values of the friction energy Ews, the friction energy Ewd and the friction energy Ewb measured under application of a given value of the input force in the transverse direction Fy, a given value of the force in the forward direction Fx+ and a given value of the force in the backward direction Fx−, respectively.

Values of the input force in the transverse direction Fy, force in the forward direction Fx+ and the force in the backward direction Fx− are determined on the basis of the RMS values of the distribution of acceleration in the transverse direction at the center of gravity position of the vehicle and the distribution of acceleration in the longitudinal direction at the center of gravity position of the vehicle in the actual use of the vehicle. The friction energy Ews, the friction energy Ewd and the friction energy Ewb described above are then obtained on the basis of the determined values of the input force in the transverse direction Fy, the force in the forward direction Fx+ and the force in the backward direction Fx− in accordance with the above formulae (10) to (12) in which the coefficients and the exponents have been decided.

Because the exponents ns, nd and nb are set at fixed values in the range of 1.5 to 3, the undetermined coefficients S, D and B can be obtained more easily in comparison with the case in which the exponents ns, nd and ns are not set at fixed values. Moreover, it is known that about the same effect (accuracy) as that obtained without setting the exponents at fixed values can be obtained.

The friction energy in the rightward turn of the vehicle is different from the friction energy in the leftward turn of the vehicle even when the force generated at the tire attached to the vehicle is the same. Moreover, the generated force varys depending on the toe angle and other factors.

It is known that the effect of the toe angle and the effect of the difference in the actual steering angle between the right wheel and the left wheel due to the Ackerman characteristic of the vehicle are the causes of the difference in the force generated in the rightward turn of the vehicle and in the leftward turn of the vehicle. Therefore, it is preferable that, using a cornering power Cp (kgf/rad), the toe angle $\theta_{toe}$ (rad) and the difference in the actual steering angle due to the Ackerman characteristic $\theta_{Ackerman}$ (rad), the input force in the transverse direction Fy is divided into two input forces, i.e., an input force in the transverse direction Fy+ generated in the rightward turn of the vehicle and an input force in the transverse direction Fy− generated in the leftward turn of the vehicle, in accordance with the following formulae (13) and (14):

$$Fy+=(Fy/2^{1/2})+[Cp\times\{\theta_{toe}+(\theta_{Ackerman}/2)\}] \qquad (13)$$

$$Fy-=(Fy/2^{1/2})-[Cp\times\{\theta_{toe}+(\theta_{Ackerman}/2)\}] \qquad (14)$$

Similarly, it is preferable that the friction energy of the tire Ews under application of a side force to the tire is divided into two friction energies, i.e., a friction energy Ews+ under application of a side force in the rightward turn of the vehicle and a friction energy Ews under application of a side force in the leftward turn of the vehicle as shown in the following formula (15):

$$Ews=Ews++Ews- \qquad (15)$$

The above difference in the actual steering angle $\theta_{Ackerman}$ due to the Ackerman characteristic is calculated as follows.

Steady driving along a circular course is simulated so that the input force in the transverse direction of the vehicle (preferably the RMS thereof) is generated during the driving at the average value of the input force obtained from the actual use of the vehicle. The radius of the assumed circular course is calculated. Then, the actual steering angles of the right wheel and the left wheel are calculated in conditions where the vehicle is driven along a circular course at the speed of 0 and both slip angles become 0 (the ideal Ackerman characteristic).

An actual vehicle exhibits an intermediate characteristic between the case where Ackerman characteristic is absent (the parallel link) and the case of the ideal Ackerman characteristic. Therefore, one half of the difference in the values calculated above is used as the difference in the actual steering angle between the right wheel and the left wheel ($\theta_{Ackerman}$) due to the Ackerman characteristic of the vehicle.

When the Ackerman characteristic of the vehicle is available, the value may be used without modification. The input force in the transverse direction Fy+ during rightward turn of the vehicle and the input force in the transverse direction Fy− during leftward turn of the vehicle may be calculated by the above computer simulation using the vehicle model with 5 or more degree of freedoms. When the computer simulation is used, the difference in the slip angle between the right wheel and the left wheel due to yawing can also be taken into consideration, so that the accuracy of the estimation can increase.

Thus, on the basis of the Ackerman characteristic and the toe angle, the friction energy Ews can be obtained as two separate friction energies which are the friction energy Ews+ during rightward turn of the vehicle to which the tire is attached and the friction energy Ews− during leftward turn of the vehicle to which the tire is attached. The friction energy Ews is obtained as the sum of the friction energy Ews+ and the friction energy Ews−, i.e., Ews++Ews−.

Therefore, a value for the friction energy Ews closer to the value in actual use can be obtained in comparison with a value for the friction energy obtained without using the Ackerman characteristic or the toe angle.

It is possible for the effects of compliance steering and other factors to be taken into consideration in addition to the effects of the Ackerman characteristic and the toe angle described above.

In the method for estimating a tire wear life of the present invention, using an input force in the transverse direction Fy+ generated during a rightward turn of the vehicle, an input force in the transverse direction Fy− generated during a leftward turn of the vehicle, a force in the forward direction Fx+ generated by the driving force, a force in the backward direction Fx− generated by the braking force, undetermined coefficients S1, S2, D and B and exponents ns1, ns2, nd and nb, the friction energy Ews+, the friction energy Ews−, the friction energy Ewd and the friction energy Ewb may be expressed by the following formulae:

$$Ews+ = S1 \times Fy+^{ns1} \quad (16)$$

$$Ews- = S2 \times Fy-^{ns2} \quad (17)$$

$$Ewd = D \times Fx+^{nd} \quad (18)$$

$$Ewb = B \times FX-^{nb} \quad (19)$$

In this case, the undetermined coefficients S1, S2, D and B and the exponents ns1, ns2, nd and nb are obtained in advance on the basis of values of the friction energy Ews+, the friction energy Ews−, the friction energy Ewd and the friction energy Ewb measured under application of a given value of the input force in the transverse direction Fy+, a given value of the input force in the transverse direction Fy−, a given value of the force in the forward direction Fx+ and a given value of the force in the backward direction Fx−, respectively.

The transverse direction, the forward direction and the backward direction are directions in relation to the direction in which the tire advances when rotated.

Values of the input force in the transverse direction Fy+, the input force in the transverse direction Fy−, the force in the forward direction Fx+ and the force in the backward direction Fx− are determined on the basis of the RMS values of a distribution of acceleration in the transverse direction at the center of gravity position of the vehicle and a distribution of acceleration in the longitudinal direction at the center of gravity position of the vehicle in the actual use of the vehicle. The above RMS values can be each obtained as the square root of the average of the square of accelerations in a given range in each distribution of acceleration.

The friction energy Ews+, the friction energy Ews−, the friction energy Ewd and the friction energy Ewb are then obtained on the basis of the determined values of the input force in the transverse direction Fy+, the input force in the transverse direction Fy−, the force in the forward direction Fx+ and the force in the backward direction Fx− in accordance with the above formulae (16) to (19) in which the coefficients and the exponents have been determined. In other words, the above energies are obtained by substituting the above determined values for the corresponding parameters in formulae (16) to (19).

Because the friction energy Ews+, the friction energy Ews−, the friction energy Ewd and the friction energy Ewb are obtained on the basis of the RMS values of the distribution of acceleration in the transverse direction at the center of gravity position of the vehicle and the distribution of acceleration in the longitudinal direction at the center of gravity position of the vehicle in the actual use of the vehicle, these friction energies are values reflecting inputs in the actual use of the vehicle. Therefore, the wear life of the tire can be estimated more accurately in comparison with the case in which the estimation is made without reflecting the input in the actual use of the tire.

In the above formulae (16) to (19) in the method for estimating a tire wear life of the present invention, each of the exponents ns1, ns2, nd and nb may set at a fixed value in the range of 1.5 to 3 in the same manner as that in formulae (10) to (12).

In this case, by setting the exponents ns1, ns2, nd and nb at fixed values in the range of 1.5 to 3, the undetermined coefficients S1, S2, D and B can be obtained more easily in comparison with the case in which the exponents ns1, ns2, nd and nb are not set at fixed values.

The wear resistance property of a tire is often evaluated on the basis of "average" values which are obtained as average values of data over the entire tire, such as an average value of the remaining groove depth of the tire tread portion and a decrease in the weight of the tire. However, when a tire is attached to a vehicle and actually used, the wear of the tire takes place unevenly in the transverse direction of the tread and the tire is often regarded to have reached the limit for disposal when the most worn portion has reached the limit for disposal even though other portions of the tire have not reached the limit for disposal. Therefore, it is preferable that the wear property of a tire is not estimated on the basis of an average value of data obtained over the entire tire but is estimated on the basis of the distribution of the amount of wear in the transverse direction of the tread.

In accordance with the method for estimating a tire wear life of the present invention, the tire wear life can be estimated at a plurality of portions of the tire. For example, by applying the measurement at a plurality of portions of the tire tread portion in the transverse direction of the tire tread portion, the distribution of the tire wear life in the transverse direction of the tire tread portion (irregular wear) can be estimated.

In the method for estimating a tire wear life of the present invention, it is preferable that the friction energy Ew is expressed as a value per unit area and unit distance of driving standardized by using a rolling radius of the tire. When the friction energy is expressed in this manner, the results of estimation of the tire wear life on a plurality of tires having different tire sizes can be compared with each other.

[The First Embodiment]

The first embodiment of the present invention will be described in detail in the following.

In the present embodiment, the friction energy Ews of a tire under application of a side force is divided into the friction energy Ews+ under application of a side force in the rightward turn of the vehicle to which the tire is attached and a friction energy Ews− under application of a side force in the leftward turn of the vehicle to which the tire is attached. The friction energy Ews is obtained as the sum of the friction energy Ews+ and the friction energy Ews−, i.e., Ews++ Ews−.

In the present embodiment, the friction energies Ews+, Ews−, Ewd and Ewb are calculated in a manner such that the input forces in the actual use of the tire are reflected.

Further, in the present embodiment, the sites of estimation are determined in advance at a plurality of positions of the tire tread portion in the transverse direction of the tire tread portion. The irregular wear at the predetermined sites of the tire tread portion in the transverse direction of the tire tread portion is estimated by calculation of the expected values of the tire wear life T1 and, where necessary, the expected values of the amount of wear, at the predetermined sites. The above mentioned expected value of the amount of wear is obtained by dividing the friction energy Ew by the rubber index Gi. The greater the expected value of the amount of wear, the greater the amount of wear.

The method for estimating the tire wear life (and occasionally the amount of wear) of a tire in accordance with the present embodiment will be described with reference to the flow charts shown in FIGS. 5A and 5B in the following. In the following descriptions of the present embodiment, the exponents ns1, ns2, nd and nb in formulae (16) to (19) are fixed at the value of 2.

Figure 10:
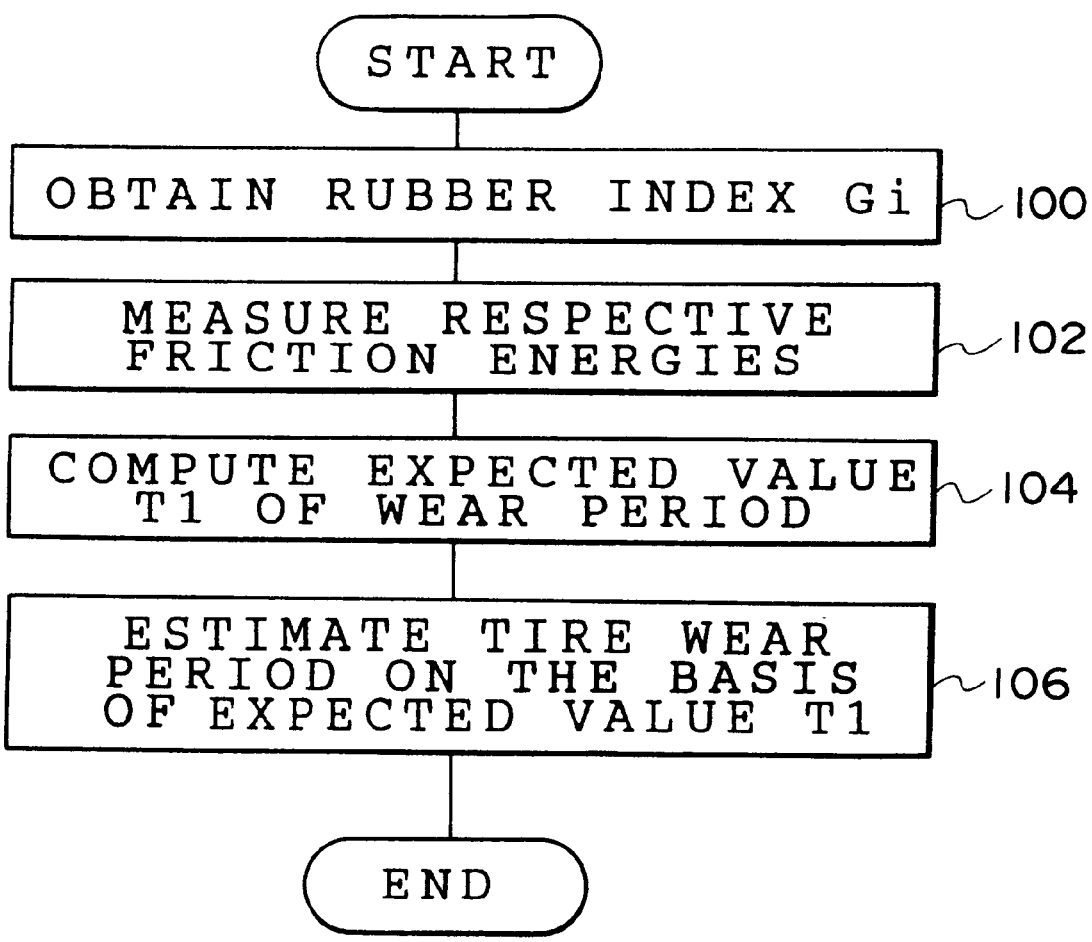
FIG. 10 shows a schematic flow chart exhibiting the procedures for estimation of the tire wear life in the third embodiment.

In step 200, in accordance with the same procedures as those conducted in step 100 of the first embodiment shown in FIG. 10, the rubber index Gi of a rubber test piece which is made of the same material as the material used in the tire tread portion of the tire (for example, a tire of a size 225/55R16) for estimation of the tire wear life or the amount of wear is obtained at a standard temperature of the atmosphere (for example, at 25° C.) under a severity approximately the same as the severity in the actual use of the tire.

In the next step 202, the friction energies Ewf and Ewa are measured at one of the predetermined sites of estimation described above using the apparatus 10 shown in FIG. 7 in accordance with the same method as that used above in step 102 of the first embodiment shown in FIG. 5.

Figure 5B:
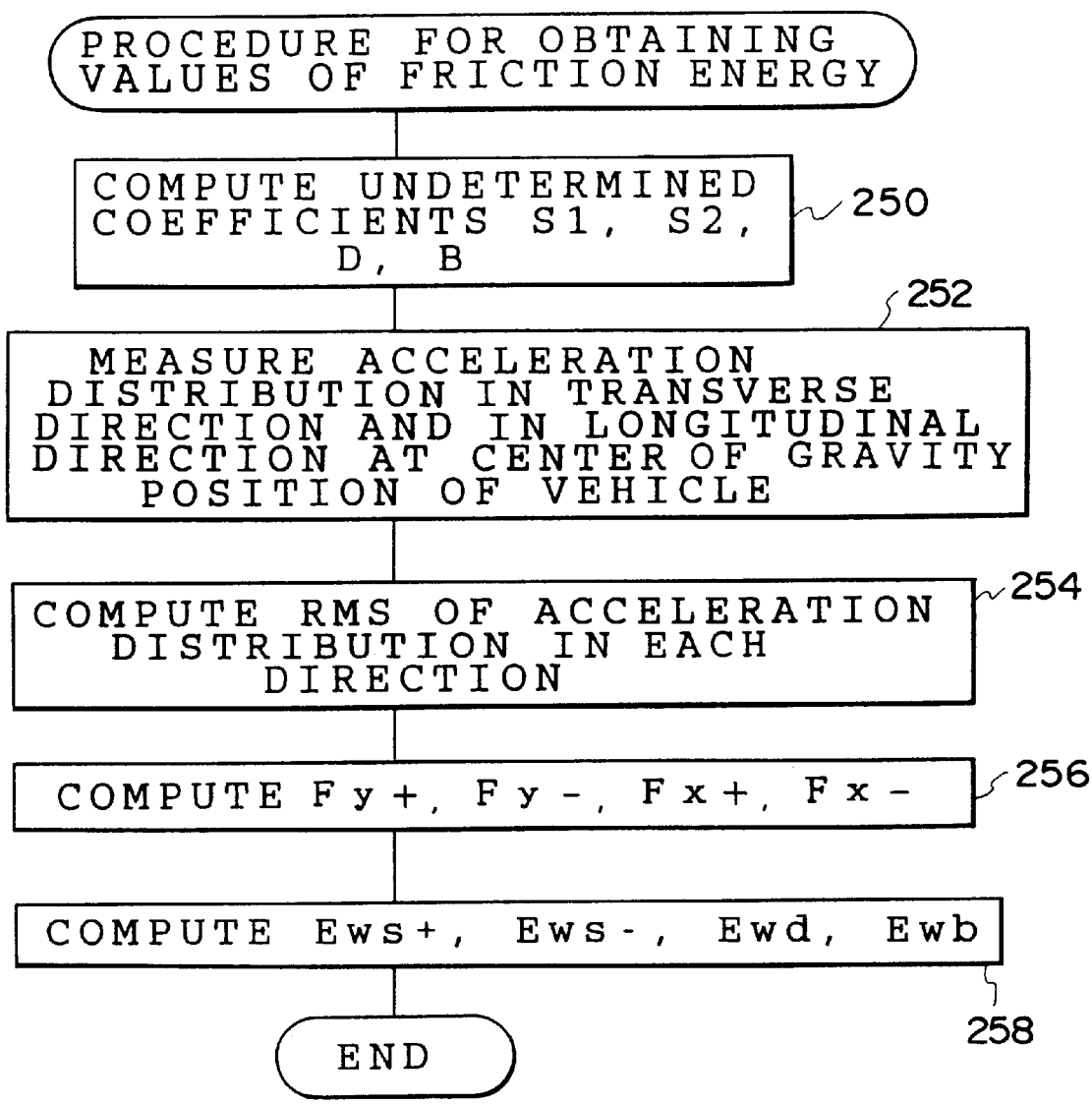
FIG. 5B shows a schematic flow chart exhibiting the procedures for obtaining the friction energies Ews+, Ews−, Ewd and Ewb in the first embodiment.

In the next step 204, in accordance with the procedures to obtain the friction energy shown by the flow chart in FIG. 5B, the friction energies Ews+, Ews−, Ewd and Ewb are obtained at the site of estimation selected from the plurality of predetermined sites of estimation in step 202 described above. This procedures for obtaining the friction energies Ews+, Ews−, Ewd and Ewb will be described in detail with reference to FIG. 5B in the following.

In step 250, using an input force in the transverse direction Fy+ in the rightward turn of the vehicle, an input force in the transverse direction Fy− in the leftward turn of the vehicle, a force in the forward direction Fx+ generated by the driving force, a force in the backward direction Fx− generated by the braking force, undetermined coefficients S1, S2, D and B and exponents ns1, ns2, nd and b, the friction energies Ews+, Ews−, Ewd and Ewb are obtained in accordance with formulae (16) to (19) described above.

The input force in the transverse direction Fy+ in the rightward turn of the vehicle, the input force in the transverse direction Fy− in the leftward turn of the vehicle, the force in the forward direction Fx+ formed by the driving force and the force in the backward direction Fx− formed by the braking force are expressed as units of kgf.

In the present embodiment, the undetermined coefficients S1, S2, D and B can be obtained, for example, by the following method. To obtain the undetermined coefficient S1, the friction energy Ews+ is measured a plurality of times (at least three times) by each time applying given values of the input force in the transverse direction Fy+ in the rightward turn of the vehicle to the tire whose wear life or amount of wear is to be estimated. Using the measured values of the friction energy Ews+ and the squares of the input forces in the transverse direction Fy+ in the rightward turn of the vehicle, a plurality of determined values of coefficients S1 are obtained by reverse calculation in accordance with formula (16), i.e., by calculation of Ews+/Fy+$^2$. The plurality of values of S1 thus obtained are averaged to obtain the value of the undetermined coefficient S1.

Similarly, to obtain the undetermined coefficient S2, the friction energy Ews− is measured a plurality of times (at least three times) by each time applying given values of the input force in the transverse direction Fy− in the leftward turn of the vehicle to the tire whose wear life or amount of wear is to be estimated. Using the measured values of the friction energy Ews− and the squares of the input forces in the transverse direction Fy− in the leftward turn of the vehicle, a plurality of determined values of coefficients S2 are obtained by reverse calculation in accordance with formula (17), i.e., by calculation of Ews−/Fy−$^2$. The plurality of values of S2 thus obtained are averaged to obtain the value of the undetermined coefficient S2.

To obtain the undetermined coefficient D, the friction energy Ewd is measured a plurality of times (at least three times) by each time applying given values of the force in the forward direction Fx+ to the tire whose wear life or amount of wear is to be estimated. Using the measured values of the friction energy Ewd and the squares of the forces in the forward direction Fx+, a plurality of determined values of coefficients D are obtained by reverse calculation in accordance with formula (18), i.e., by calculation of Ewd/Fx+$^2$. The plurality of values of D thus obtained are averaged to obtain the value of the undetermined coefficient D.

To obtain the undetermined coefficient B, the friction energy Ewb is measured a plurality of times (at least three times) by each rime applying given values of the force in the backward direction Fx− to the tire whose wear life or amount of wear is to be estimated. Using the measured values of the friction energy Ewb and the squares of the forces in the backward direction Fx−, a plurality of determined values of coefficients B are obtained by reverse calculation in accordance with formula (19), i.e., by calculation of Ewb/Fx−$^2$. The plurality of values of B thus obtained are averaged to obtain the value of the undetermined coefficient B.

Figure 7:
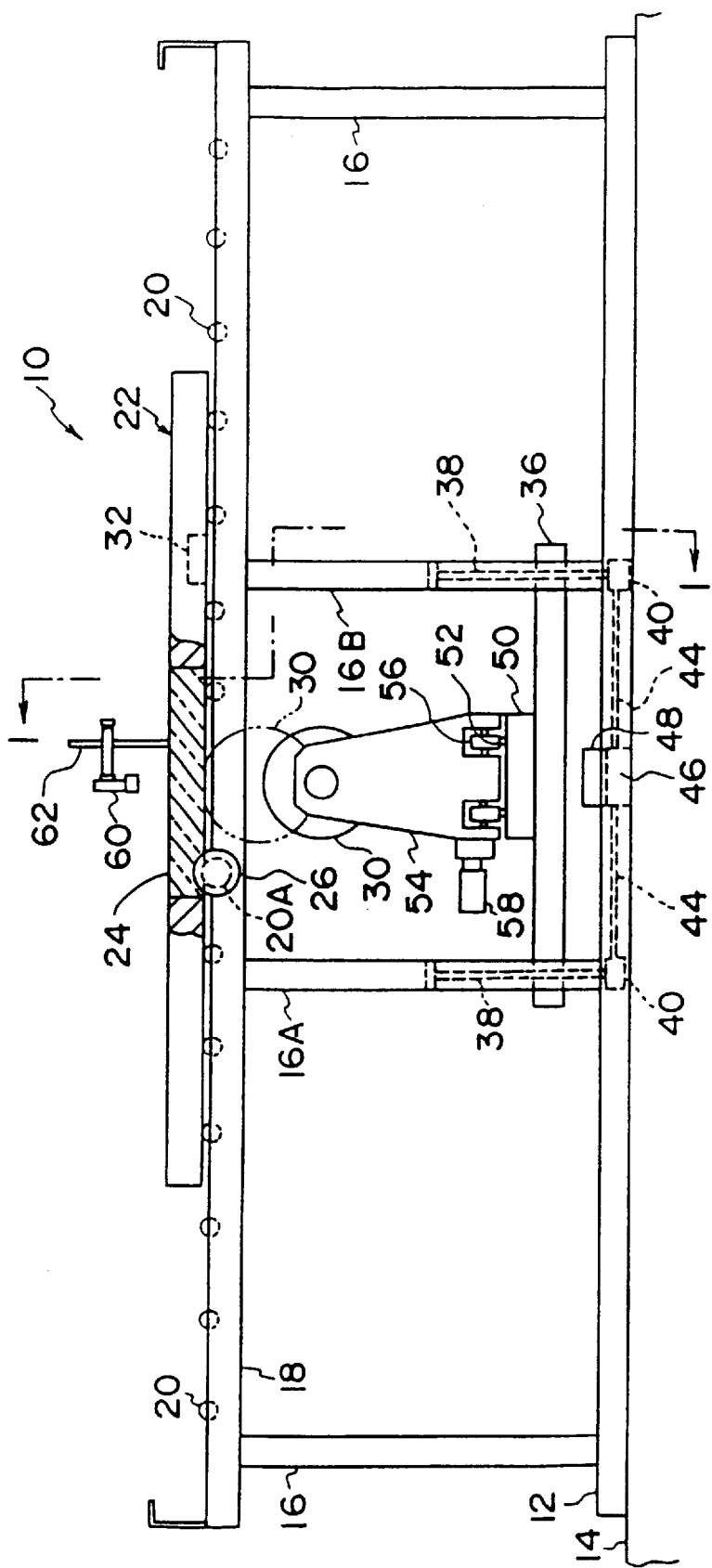
FIG. 7 shows a side view of an apparatus for measuring parameter values at a road-contacting portion of a tire tread used for measuring friction energies in the embodiments of the present invention

The friction energies Ews+, Ews−, Ewd and Ewb are measured, for example, by using the apparatus 10 shown in FIG. 7.

Figure 6:
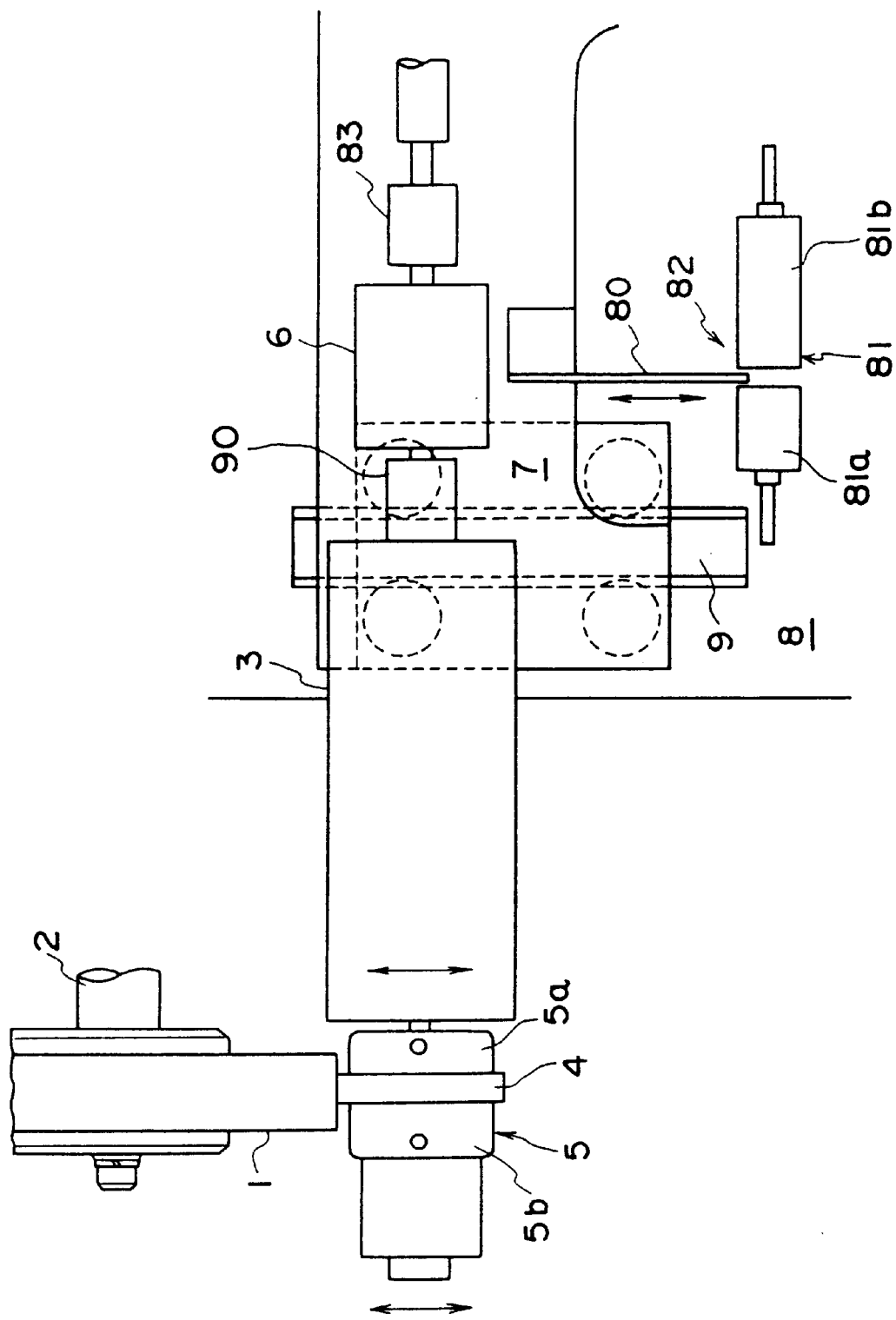
FIG. 6 shows a plan view of the main portion of an abrasion tester used for measuring the rubber index Gi in the embodiments of the present invention.

The measurement of the rubber index Gi can be conducted by using an abrasion tester. The main portion of an example of such a tester is shown in FIG. 6. The abrasion tester shown in the figure has a construction utilizing the Lambourn abrasion tester and is equipped with a shaft 2 for driving a grindstone having a rotatable grindstone 1 at one end portion. The grindstone 1 is a rotating body and is used as a model of the road surface. The other end portion of the shaft 2 for driving a grindstone is connected to a driving means of rotation such as a servomotor which is not shown in the figure. The grindstone 1 is rotated by the driving means for rotation via the shaft 2 for driving a grindstone at an angular speed of ωd (rad/min).

A shaft 3 for driving a rubber test piece is disposed extending parallel to the shaft 2 for driving a grindstone. At one end portion of the shaft 3 for driving a rubber test piece, a holder 5 for holding a rubber test piece 4 having a round disk shape is disposed. The other end portion of the shaft 3 for driving a rubber test piece is connected to a driving means of rotation such as a servomotor which is different from the above mentioned driving means for rotation and is not shown in the figure. Between both end portions, a coupling which allows change in angle (a universal coupling) 90, a clutch 6 and a torque meter 83 are disposed.

The holder 5 is composed of a receiving pad 5a disposed at the side of the shaft 3 for driving a rubber test piece and a clamp pad 5b which can move forward and backward with respect to the receiving pad 5a by a cylinder disposed at a position directly below the shaft 3 for driving a rubber test piece. The pads 5a and 5b hold the rubber test piece 4 disposed between the pads from both sides of the rubber test piece in the direction of the thickness by a given force and places the circumferential surface of the rubber test piece 4 at a position facing the circumferential surface of the grindstone 1. Therefore, when the shaft 3 for driving a rubber test piece rotates, the rubber test piece 4 rotates together with both pads 5a, 5b at the same speed as the speed of the shaft 3.

The clutch 6 transfers the rotating force of the driving means of rotation to the shaft 3 for driving a rubber test piece when the clutch 6 is engaged. When the clutch 6 is released, the rotating force of the driving means of rotation is not transferred to the shaft 3 for driving a rubber test piece and the rubber test piece is rotated freely.

The shaft for driving a rubber test piece 3 is fixed on a movable base 7. The movable base is attached to guide rails 9 disposed on a fixed base 8 in a direction perpendicular to the shaft 3 for driving a rubber test piece in a manner such that the movable base 7 can move forward and backward along the rails 9. Therefore, the shaft 3 for driving a rubber test piece can move closer to or away from the shaft 2 for driving a grindstone while the axes of both shafts are held parallel with each other.

The movable base 7 is moved by an apparatus for applying a load which is not shown in the figure. The grindstone 1 and the rubber test piece 4 can be pressed to each other by the movement of the movable base 7. When the grindstone 1 and the rubber test piece 4 are pressed to each other, a longitudinal force is applied to the rubber test piece 4. The longitudinal force can be detected by a force component meter 89 (refer to FIG. 12).

The longitudinal force means a force in the tangential direction on the surface of contact between the grindstone 1 and the rubber test piece 4. The force is perpendicular to the plane of the paper on which FIG. 6 is printed.

A laser displacement meter (a displacement sensor) 82 composed of a light shielding plate 80 and a sensor head 81 is provided to detect the amount of displacement of the movable base 7 relative to the fixed base 8 as shown. The light shielding plate 80 is attached to the movable base 7 and the sensor head 81 is attached to the fixed base 8.

The laser light is emitted from a light emitting portion 81a of the sensor head 81 and received by a light receiver 81b. A received amount of layer light changes depending on the area of the sensor head 81 shielded by the intrusion of the light shielding plate 80 attached to the movable base 7. Based on this change in the amount of light, the displacement sensor 82 detects the amount of displacement of the movable base 7 relative to the fixed base 8 and measured from a reference position.

The reference position of the movable base 7 is the position of the movable base 7 relative to the fixed base 8 when the movable base is placed in a manner such that the distance between the central axis line of the rubber test piece 4 and the circumferential surface of the grindstone 1 (the surface closer to the rubber test piece 4) is equal to the theoretical radius of the rubber test piece 4.

Figure 8B:
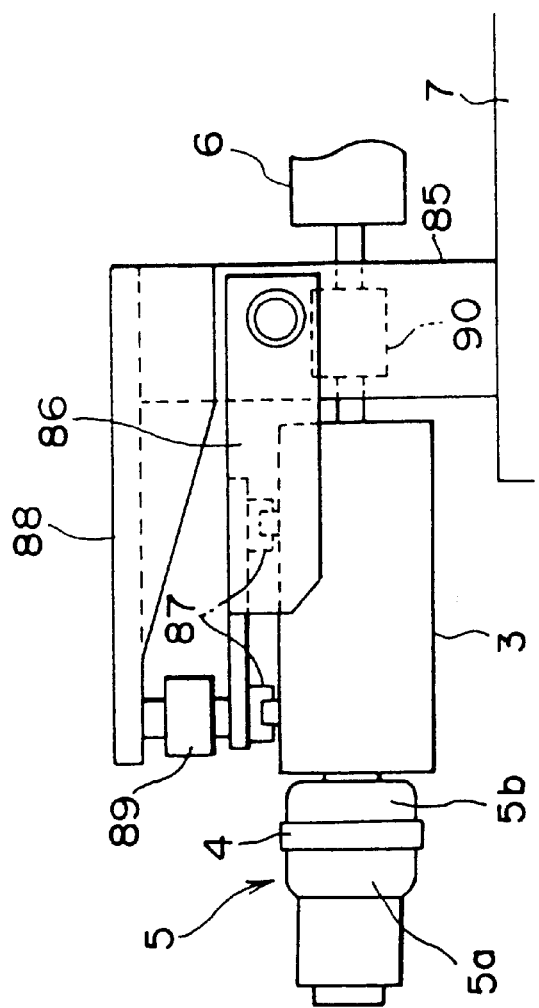
FIG. 8B shows a side view in the direction A of the portion of the apparatus shown in FIG. 8A.
Figure 8A:
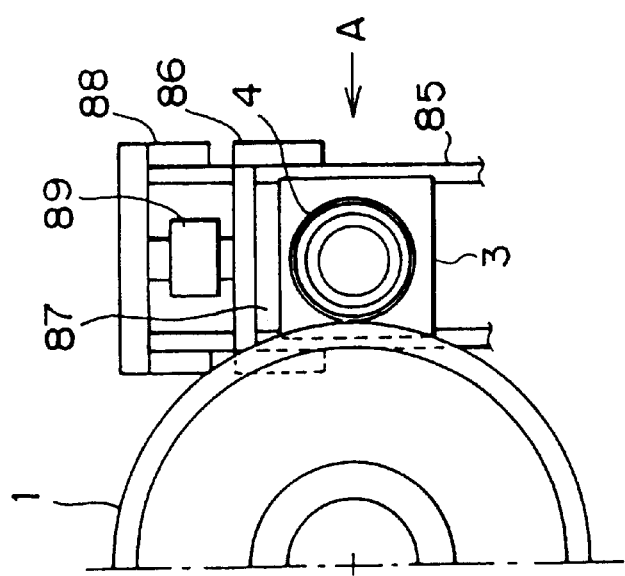
FIG. 8A shows a side view exhibiting a portion for measuring the longitudinal force in the apparatus shown in FIG. 7.

As shown in FIGS. 8A and 8B, in the present embodiment, a pair of brackets 85 are disposed protruding upward on the movable base 7 in a manner such that the coupling which allows change in the angle 90 is placed between the pair of brackets 85. A swinging arm 86 is attached at the upper end portions of the brackets 85, such that one end of the swinging arm 86 is swingably supported at the upper end portions of the brackets 85 and the other end of the swinging arm 86 is engaged with the shaft 3 for driving a rubber test piece (more particularly, with the shaft 3 for driving a rubber test piece at a portion closer to the free end portion than the position of the coupling which allows change in the angle 90). Due to the above construction, the swinging arm 86 can make a vertical swinging displacement accurately following the movement of the shaft 3 for driving a rubber test piece.

It is preferable that the engagement of the swinging arm 86 with the shaft 3 for driving a rubber test piece is made via a ball slide unit 87 which allows a relative displacement between the swinging arm and the shaft in the horizontal direction. It is preferable that an intermediate portion of the swinging arm 86 is also engaged with the shaft 3 for driving a rubber test piece via a similar slide unit. Due to this construction, constraints applied to the force component meter 89 due to the pressure of the rubber test piece 4 on the grindstone 1 caused by the movement of the movable base 7 are removed and the longitudinal force on the rubber test piece alone can be detected correctly.

A fixed arm 88 having a great rigidity is disposed at the upper ends of the brackets 85 in the horizontal direction toward the free end portion of the shaft 3 for driving a rubber test piece. Between the fixed arm 88 and the swinging arm 86, the force component meter 89 is disposed to detect the force in the direction intersecting the driving shaft, i.e., in the vertical direction in the figure.

Due to the above construction, the longitudinal force generated on the rubber test piece 4 as described above can be smoothly transferred to the force component meter 89 via the shaft 3 for driving a rubber test piece 3 and the swinging arm 86. Thus, the longitudinal force can be detected with great accuracy.

In the present embodiment, a conventional load cell can be used as the force component meter 89. Therefore, due to the excellent durability of the load cell, the great accuracy of the measurement can be maintained for a long time without the possibility of failure or the necessity for maintenance and there is no possibility of decrease in the durability of constituent parts such as the driving shaft. In addition, as the driving shaft does not have constrictions, rigidity of the driving shaft is increased and the trouble of a bouncing sample does not occur.

Figure 9A:
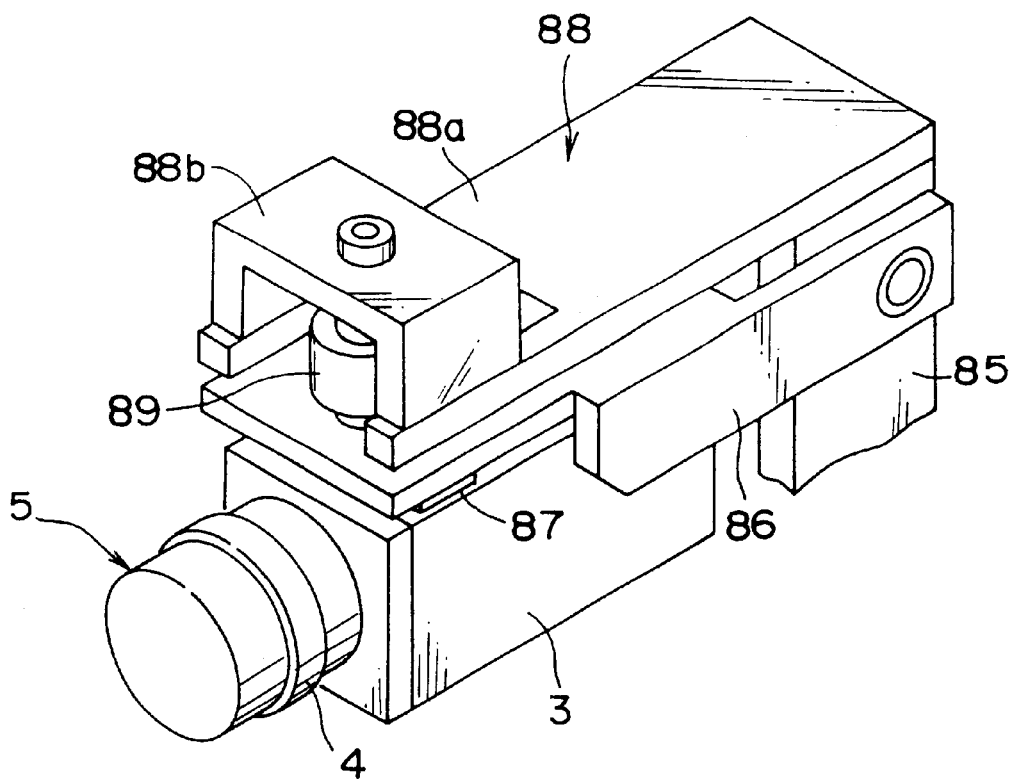
FIG. 9A shows a perspective view of a modification of the portion of the apparatus fir measuring the longitudinal force shown in FIG. 8A
Figure 9B:
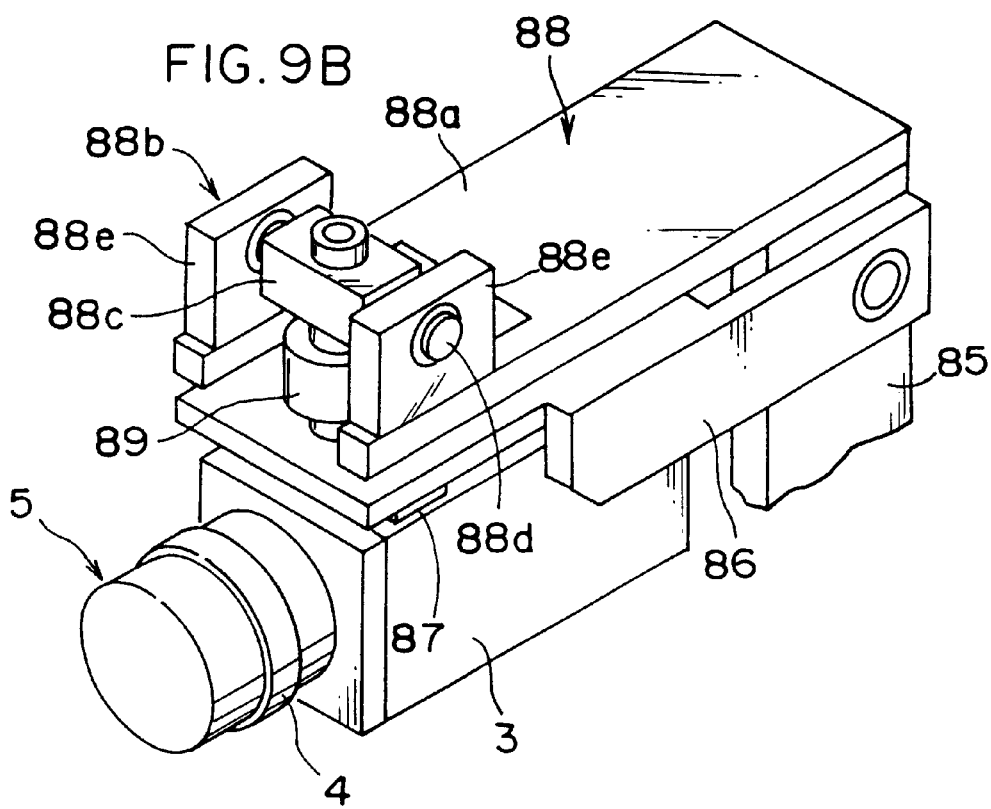
FIG. 9B shows a perspective view of another modification of the portion of the apparatus for measuring longitudinal force shown in FIG. 8A.

FIGS. 9A and 9B show perspective views of modifications of the main portion of the apparatus for measuring longitudinal force including the force component meter 89. FIG. 9A shows a construction in which the force component meter 89 is disposed between an end portion of the swinging arm 86 engaged with the shaft 3 for driving a rubber test piece and a gate-shaped protrusion 88b of the fixed arm 88 which protrudes upward from the main portion 88a at the end portion of the fixed arm 88.

In this modification, when the force component meter 89 disposed at the gate-shaped protrusion 88b, as well as the swinging arm engaged with the coupling which allows change in the angle, are subjected to a great load of pressure in the direction perpendicular to the longitudinal direction, the force component meter is protected by the gate-shaped protrusion 88b and is not affected by the force. Due to this, the modification shown in FIG. 9A has an advantage in comparison with the apparatuses shown in FIGS. 6, 8A and 8B.

In the apparatus shown in FIG. 9B, horizontal shafts 88d are disposed protruding at end portions of the portion 88c which corresponds to the top wall portion of the gate-shaped protrusion 88b shown in FIG. 9A and both end portions of the horizontal shaft 88d are supported by bearings at the portions corresponding to the side wall portions 88e.

In this construction, the portion 88c which corresponds to the top wall portion suppresses displacement of the horizontal shaft 88*d* in the axial direction, i.e., in the horizontal direction perpendicular to the axial direction of the shaft 3 for driving a rubber test piece, and the horizontal displacement caused by the load applied in the direction perpendicular to the longitudinal direction is prevented. To sensitively detect the friction force in the longitudinal direction generated at the sample, a bearing is disposed at the connecting portion between the portion 88*e* which corresponds to the side wall portion and the portion 88*c* which corresponds to the top wall portion of the gate-shaped protrusion 88*b*. Due to this bearing, displacement by rotation of the portion 88*e* which corresponds to the side wall portion around the axis line of the horizontal shaft 88*d* is facilitated. Moreover, a ball slide unit is disposed at the lower side of the fixed arm 88. Thus, the force component meter can detect the friction force generated at the sample more accurately.

The method for measuring the rubber index Gi by using the above abrasion tester will be described in detail in the following.

The mass m1 of the rubber test piece 4 is measured. The rubber test piece 4 is held by the holder 5. While the clutch 6 at the shaft 3 for driving a rubber test piece is released, the shaft for driving a rubber test piece (actually a movable base 7) is moved toward the shaft 2 for driving a grindstone 2 by the above mentioned apparatus for applying a load. As a result, the circumferential surface of the rubber test piece 4 can be pressed against the circumferential surface of the grindstone 1 at a given pressure. When the grindstone 1 is rotated at an angular speed of $\omega d$ by a means for rotation, the rubber test piece 4 rotates at the slip ratio of 0 (slaved rotation) by the friction force of the grindstone 1 since the clutch 6 is released and the rubber test piece 4 can rotate freely. The longitudinal force $F_0$ is detected by the force component meter 89.

The distance between the axis line of rotation of the rubber test piece 4 and the circumferential surface of the grindstone during the slaved rotation of the rubber test piece 4 is obtained from the amount of displacement of the movable base 7 relative to the reference position which is detected by the displacement sensor 82. The obtained distance is regarded as the effective radius under dynamic load Rr of the rubber test piece 4. In other words, the effective radius under dynamic load Rr is the actual radius of the portion of the rubber test piece 4 pressed against the grindstone 1 during the testing.

There is a possibility that the distance between the axis line of rotation of the rubber test piece and the circumferential surface of the grindstone may very depending on the position of contact in the circumferential direction of the rubber test piece 4 and the grindstone 1 due to fluctuations in the shape during the molding of the rubber test piece or other causes. The effect of this difference can be suppressed by measuring the distance a plurality of times during the rotation of the rubber test piece 4 and taking the average of the measured values.

It is possible for an effective rolling radius to be used in place of the effective radius under dynamic load.

Next, on the basis of the effective radius under dynamic load Rr of the rubber test piece 4 obtained as described above, the slip ratio S is selected in the range of 0.5 to 5% and preferably in the range of 1 to 3% (for example, 2% which is defined as $S_0$) in accordance with the following formula (20):

$$S = \frac{\omega_d R_d - \omega_s R_r}{\omega_s R_r} \times 100(\%) \qquad \text{formula (20)}$$

wherein $\omega s$ represents the angular speed of the rubber test piece (rad/min) and Rd represents the radius of the rotating grindstone 1.

In the present wear test, after the clutch 6 at the shaft 3 for driving a rubber test piece is connected, the selected slip ratio can be achieved by setting the difference between the circumferential speed of the grindstone 1 ($\omega d \times Rd$) and the circumferential speed of the rubber test piece 4 ($\omega s \times Rr$) at a value satisfying formula (20) by using a means for rotation. The slip ratio S can be set at $S_0$ by rotating the rubber test piece 4 at an angular speed $\omega s$ obtained in accordance with the following formula (21):

$$\omega_s = \frac{R_d}{R_r} \cdot \frac{100}{100 + S_o} \cdot \omega_d \qquad \text{formula (21)}$$

The test is conducted by setting the slip ratio at a value in the range of 0.5 to 5% because a friction energy at a severity approximately the same as the severity in actual use can be achieved with the rubber test piece 4 in that condition.

When the slip ratio exceeds 5%, the form of wear begins to show elastic wear which is different from the form shown in the actual use of the vehicle and such a slip ratio is not preferable. When the slip ratio is less than 0.5%, the testing requires a long time and the amount of wear decreases to resulting in insufficient accuracy of the test. In view of the possibility of error occurring in the test, the slip ratio is preferably selected in the range of 1 to 3% and it is more preferable that the slip ratio is set at 2%.

As described above, the effective radius under dynamic load Rr is actually obtained in the test of the rubber test piece 4 and the slip ratio is selected on the basis of the obtained effective radius under dynamic load Rr. Therefore, the slip ratio can be set with a high accuracy at any value of the slip ratio and the accuracy of the test in the present wear test can be significantly improved.

The rubber test piece 4 and the grindstone 1 are rotated at the slip ratio of $S_0$ for a given time. The longitudinal force $F_1$ is detected by the force component meter 89 during the rotation at the slip ratio of $S_0$. The rubber test piece 4 is released from the holder 5 and the mass m2 of the test piece 4 is measured.

The friction energy ew (kgf/cm$^2$) per unit area and unit distance of driving is obtained by using the longitudinal force $F_0$ obtained at the slip ratio of 0 (in the free rolling, i.e., when the rubber test piece is allowed to roll freely), the longitudinal force F1 obtained at the slip ratio of $S_0$ and the slip ratio $S_0$ in accordance with the following formula (22):

$$ew = (F1 - F0) \cdot S_0 / (2\pi Rr \cdot D) \qquad (22)$$

The wear depth (mm/1000 km) is calculated by using the amount of wear $W_0$ (=m1−m2) (g) obtained by the measurement in accordance with the following formula (23):

$$W = \frac{W_o \cdot 10^9}{\rho \cdot (V_d \cdot t) \cdot (2\pi R_r \cdot D)} \qquad \text{formula (23)}$$

wherein $\rho$ (g/cm$^3$) represents the density of the sample, t (min) represents the time duration of the test, D (cm) represents the width of the sample and Vd (cm/min) represents the circumferential speed of the grindstone 1.

The rubber index Gi is obtained in accordance with formula (8) described above from the friction energy ew per unit area and per unit distance of driving and the wear depth W obtained in accordance with formulae (22) and (23), respectively.

After the rubber index Gi is obtained as described above, in step 102 in FIG. 10, the friction energy of the tire Ewf in free rolling, the friction energy of the tire Ewa when the tire is given a toe angle, the friction energy of the tire Ews under application of a side force to the tire, the friction energy of the tire Ewd under application of a driving force to the tire and the friction energy of the tire Ewb under application of a braking force to the tire are obtained with the tire whose tire wear life is to be estimated. The friction energies Ewf, Ewa, Ews, Ewd and Ewb are friction energies expressed as values per unit area and unit distance of driving standardized by using the rolling radii of the tires and are expressed by the unit of kgf/cm².

The measurement of the friction energies can be conducted by using, for example, an apparatus 10 for measuring the values required for calculating the friction energies generated at the road-contacting portion of a tire tread shown in FIG. 7 which is described in the specification of Japanese Patent Application Laid-Open No. (abbreviated as JP-A, hereinafter) 7-63658.

Using the apparatus for measuring the parameter values at the road-contacting portion 10 of a tire tread, the amount of slip S (cm) is measured in free rolling, in a state in which the tire having a toe angle, in a state in which a side force is applied to the tire, in a state in which a driving force is applied to the tire and in a state in which a braking force is applied to the tire. At the same time, the shearing force τ (kgf/cm²) is measured by using a converter of three force components 32 disposed on the road surface 22. As described in the specification of JP-A 7-63658, the amount of work of friction E at the road-contacting surface of a tire is expressed by the following formula (24):

$$E = \int \tau d \cdot s \qquad (24)$$

Accordingly, the amount of work of friction at the road-contacting surface of the tire is calculated by using the amount of slip S and the shearing force τ obtained by the measurement using the apparatus 10 in accordance with formula (24), and the obtained value is used as the friction energy.

In the measurement of the friction energy Ewa, the toe angle can be provided by attaching a tire 30 to an upper portion of the tire support 54 in a manner such that the angle of the equitorial line of the attached tire 30 with respect to the direction of movement is set at the desired toe angle. A camber angle may also be provided, where necessary.

The side force is applied by moving the tire support 54 rightward or leftward with respect to the direction of movement of the road surface 22 while the road surface 22 is moving (rotating) or by setting an angle between the direction of the movement of the road surface 22 and the face of the wheel.

The method for measurement of the amount of slip S and the shearing force τ of the road-contacting portion of a tire tread using the apparatus 10 will be described in detail in the following.

When the amount of slip S at a particular position (for example, a block) in the road-contacting portion is to be measured, the particular portion on the tire tread is marked. The tire 30 is rotated so as to place the marked block at the upper portion of the tire. The position of the tire support 54 is adjusted so that the marked portion of the tire is brought to a position directly below a television camera 60. The road surface 22 is moved so that the central position of a transparent plate 24 is brought to the position directly above the marked portion. A subframe 36 is raised to press the tire tread against the transparent plate 24 of the road surface 22. To determine the pressure of the tire 30, the road surface 22 is moved so that the tire 30 is brought into contact with a converter of three force components 32 and the measurement and adjustment are made.

The road surface 22 is brought to one side of a horizontal frame 18 in the longitudinal direction. Then, the road surface 22 is moved to the other side of the horizontal frame 18 in the longitudinal direction at a given speed, for example, at the circumferential speed of the tire.

By the above procedure, any particular marked portion in the tire tread can be continuously observed at the center of the finder area of the television camera 60 from the time in which the particular portion is brought into contact with the transparent plate 24 through the time when the particular portion leaves the transparent plate 24.

In the apparatus 10, the television camera 60 is fixed to the road surface 22. Therefore, when there is no slipping of the particular portion contacting the transparent plate 24 of the road surface 22, the marked portion is observed as a fixed portion at the center of the television monitor.

When the particular portion contacting the transparent plate 24 does slip, the position of the selected portion shows a shift relative to the transparent plate 24. Therefore, the marked portion observed in the television monitor moves from the central position of the monitor and the amount of the movement is measured to obtain the amount of slip S.

Using the apparatus 10, the condition of the tire tread can be easily monitored from the time in which the particular portion of the tread is brought into contact with the transparent plate 24 of the road surface 22 through the time when the particular portion is separated from the transparent plate 24.

In the apparatus 10, it is not necessary for the image of the entire road-contacting surface to be recorded. Accordingly, the entire finder area of the television camera 60 can be used for analyzing the image of a small region to be measured (for example, the entire finder area may be used for analyzing one block of the tread) so that the amount of slip S can be measured more accurately.

The shearing force τ applied to the road-contacting surface is measured by using the converter of three force components 32 disposed on the road surface 22.

After the friction energies are measured as described above, in step 104 shown in FIG. 10, the expected value of the wear life T1 of the tire can be calculated by using the values of the rubber index Gi measured in step 100, the friction energies measured in step 102 and the groove depth NSD of the tire in formula (9). In the first embodiment, the groove depth NSD of the tire is measured in advance as the average value of the values of the groove depths measured at a plurality of positions of the tire tread portion. The friction energy Ew used in formula (9) is obtained in accordance with formula (6).

In the present embodiment of the method for estimating a tire wear life, using an input force in the transverse direction Fy+ generated during a rightward turn of the vehicle, an input force in the transverse direction Fy− generated during a leftward turn of the vehicle, a force in the forward direction Fx+ generated by the driving force, a force in the backward direction Fx− generated by the braking force, undetermined coefficients S1, S2, D and B and exponents ns1, ns2, nd and nb, the friction energy Ews+, the friction energy Ews−, the friction energy Ewd and the friction energy Ewb may be expressed by the following formulae as above described:

$$Ews+ = S1 \times Fy+^{ns1} \quad (16)$$

$$Ews- = S2 \times Fy-^{ns2} \quad (17)$$

$$Ewd = D \times Fx+^{nd} \quad (18)$$

$$Ewb = B \times FX-^{nb} \quad (19)$$

Referring to FIGS. 5A and 5B, at step 200, a rubber index Gi as in the same manner as step 100. At step 202, Ewf and Ewa are obtained in the same manner as step 102. At step 204, Ews+, the friction energy Ews−, the friction energy Ewd and the friction energy Ewb are obtained.

Specifically, at step 250, Ews+, Ews−, Ewd and Ewb are obtained according to the method described above using the formulae (16)–(19). The undetermined coefficients S1, S2, D and B are also obtained as described above. Herein, Ews+, Ews−, Ewd and Ewb may be obtained in a state in which the camber angle, the toe angle are provided at the tire.

Figure 11:
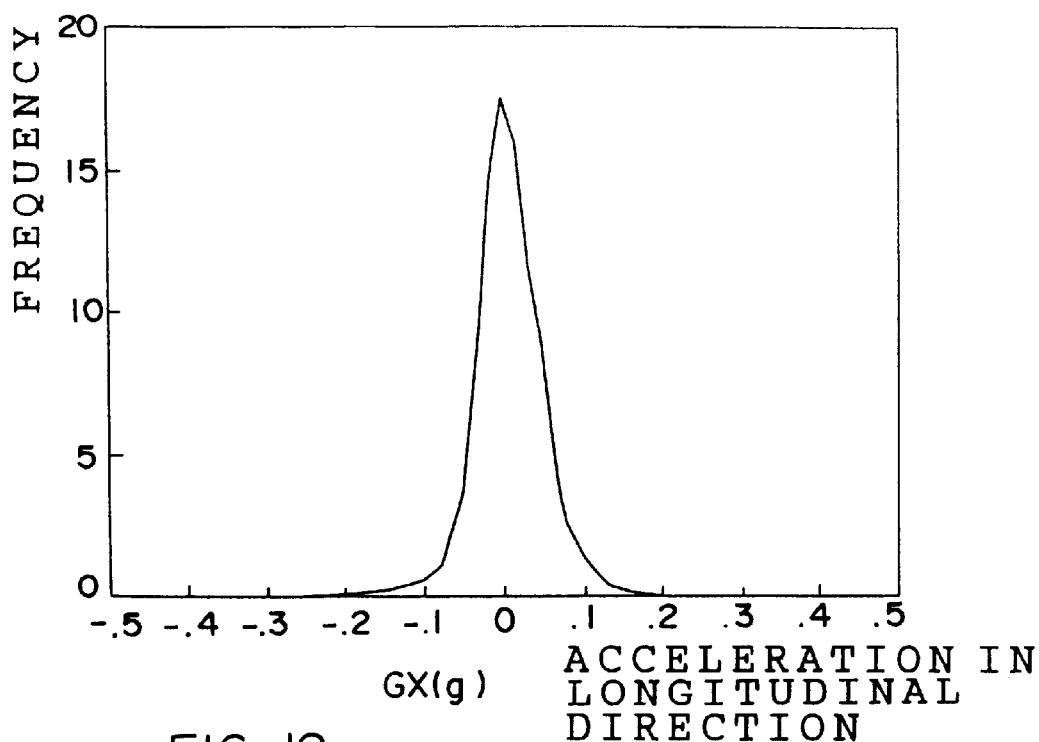
FIG. 11 shows a graph exhibiting an example of the distribution of acceleration in the longitudinal direction at the center of gravity position of a vehicle in actual use.
Figure 12:
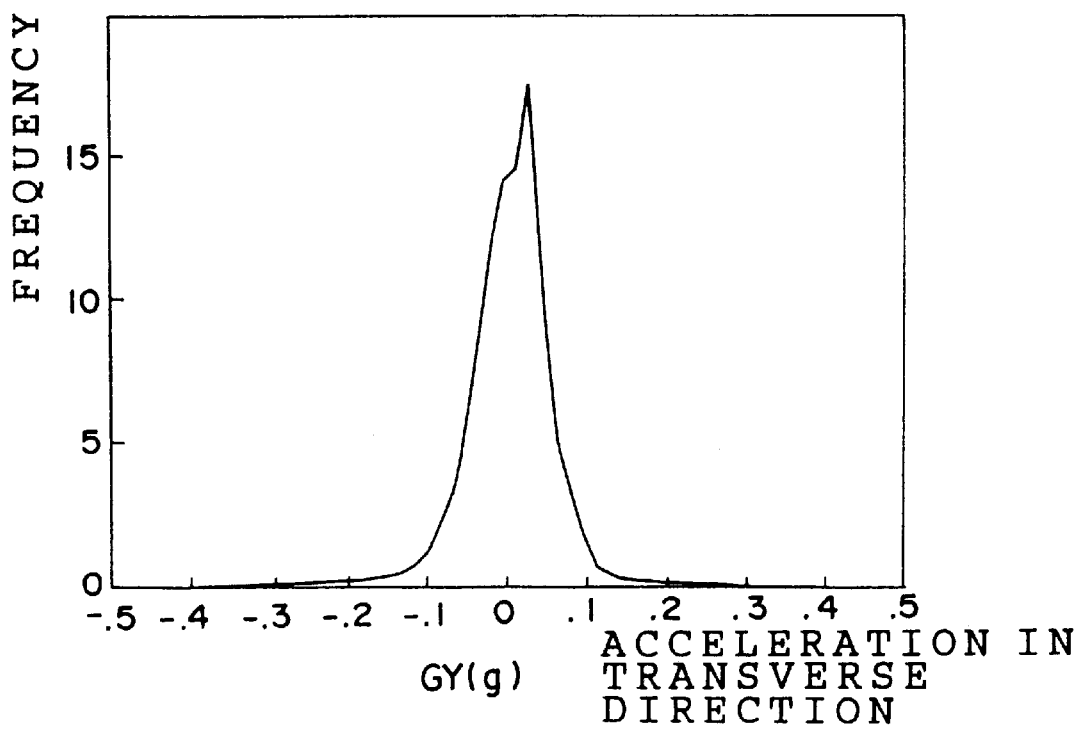
FIG. 12 shows a graph exhibiting an example of the distribution of acceleration in the transverse direction at the center of gravity position of a vehicle in actual use.

In the next step 252, roads which represent the conditions in the actual use of a tire in the estimation of the wear life or the amount of wear (for example, generally used roads in Japan) are specified. A vehicle is driven on the specified roads for a given distance and the acceleration (G) in the transverse direction at the center of gravity position of the vehicle and the acceleration (G) in the longitudinal direction at the center of gravity position of the vehicle are measured at a given time interval to obtain the distribution of the acceleration in the transverse direction at the center of gravity position of the vehicle and the distribution of the acceleration in the longitudinal direction at the center of gravity position of the vehicle. These accelerations can be measured, for example, by a G sensor disposed at the center of gravity position of the vehicle. An example of the distribution of the acceleration in the longitudinal direction at the center of gravity position of the vehicle is shown in FIG. 11 and an example of the distribution of the acceleration in the transverse direction at the center of gravity position of the vehicle is shown in FIG. 12.

In the next step 254, the RMS value of the distribution of the acceleration in the transverse direction (As), the RMS value Ax+ of the distribution of the acceleration in the forward direction and the RMS value Ax− of the distribution of the acceleration in the backward direction are calculated. These values are calculated so that Fy, Fx+ and Fx− can be calculated in the next step 256.

The RMS value is a value obtained as the square root of the average of the square of values in a given range of the distribution of the acceleration. When the RMS value Ax+ of the distribution of the acceleration in the forward direction is to be obtained, the values of acceleration greater than 0 in the distribution of acceleration in the longitudinal direction at the center of gravity position of the vehicle are used. When the RMS value Ax− of the distribution of the acceleration in the backward direction is to be obtained, the values of acceleration smaller than 0 in the distribution of acceleration at the center of gravity position of the vehicle in the longitudinal direction are used.

In the next step 256, the input force in the transverse direction Fy, the input force in the forward direction Fx+ and the input force in the backward direction Fx− are obtained from the RMS values of As, Ax+ and Ax− obtained above and the load applied to the tire w in accordance with the following formulae (27) to (29):

$$Fy = w \times As \quad (27)$$

$$Fx+ = w \times Ax+ \quad (28)$$

$$Fx- = w \times Ax- \quad (29)$$

wherein the load applied to the tire is expressed by the unit of kg.

In the calculation of the force in the forward direction Fx+ for a vehicle having only two driving wheels, the sum of forces generated by the two driving wheels is made equal to the force of inertia at the center of gravity position of the vehicle because the force for accelerating the entire vehicle must be generated by the two driving wheels alone.

The above Fx+, Fx− and Fy (Fy+, Fy−) may also be obtained by computer simulation of the vehicle under virtual conditions which would give the RMS values as above.

The input force in the transverse direction Fy+ in the rightward turn of the vehicle and the input force in the transverse direction Fy− in the leftward turn of the vehicle in which the toe angle and the Ackerman characteristics are taken into consideration are obtained from the above input force in the transverse direction Fy in accordance with formulae (13) and (14).

In the next step 258, the friction energy Ews+ is obtained by using the coefficient S1 and the input force in the transverse direction Fy+ which have been obtained in formula (16). The friction energy Ews− is obtained by using the coefficient S2 and the input force in the transverse direction Fy− which have been obtained in formula (17). The friction energy Ewd is obtained by using the coefficient D and the force in the forward direction Fx+ which have been obtained in formula (18). The friction energy Ewb is obtained by using the coefficient B and the force in the backward direction Fx− which have been obtained in formula (19).

When the friction energies Ews+, Ews−, Ewd and Ewb are obtained as described above, it is decided in step 205 in FIG. 5A whether the tire wear life is estimated or not.

When the tire wear life is estimated, in step 206, the groove depth NSD is measured in the vicinity of the site of estimation. In the next step 208, the rubber index Gi obtained in step 200, the friction energies Ewf and Ewa obtained in step 202, the friction energies Ews+, Ews−, Ewd and Ewb obtained in step 204 and the groove depth NSD obtained in step 206 are used in formula (9) and the expected value of the tire wear life T1 at this site of estimation is calculated.

The friction energy Ews used for calculation of the friction energy Ew is obtained as the sum of the friction energy Ews+ and the friction energy Ews−, i.e., as Ews++ Ews−.

After the expected value T1 of the tire wear life is calculated, in the next step 210, it is examined whether the expected values of the tire wear life have been calculated at all of the plurality of the predetermined sites of estimation. When any sites where the calculation has not been made are found, the expected values of the tire wear life are calculated at the sites where the calculation has not been made in accordance with the above steps 202 to 208 and then the procedures are completed.

The tire wear life at each site of estimation may be estimated by using the expected value T1 of the tire wear life at each position. The average tire wear life of the entire tire may be estimated by using the average value of the expected values of the tire wear life obtained at individual sites of estimation.

When it is decided in step 205 that the tire wear life is not estimated, the decision is regarded to mean that the amount of wear is estimated and the procedure in step 212 is conducted. The expected value of the amount of wear at a specific site of estimation is calculated on the basis of the rubber index Gi obtained in step 200, the friction energies Ewf and Ewa obtained in step 202 and the friction energies Ews+, Ews−, Ewd and Ewb obtained in step 204.

The expected value of the amount of wear is obtained by dividing the friction energy Ew by the rubber index Gi as described above. The greater the expected value of the amount of wear, the greater the amount of wear.

More specifically,

Expected value of the amount of wear

=Ew/Gi

={(Ewf)+(Ewa)+(Ews+)+(Ews−)+(Ewd)+(Ewb)}/Gi

After the expected value of the amount of wear is calculated, in the next step 214, it is examined whether the expected values of the amount of wear have been calculated at all of the plurality of the predetermined sites of estimation. When any sites where the calculation (computation) has not been made are found, the expected values of the amount of wear are calculated at the sites where the calculation has not been made in accordance with the above steps 202 to 214 and then the procedures are completed.

Figure 13A:
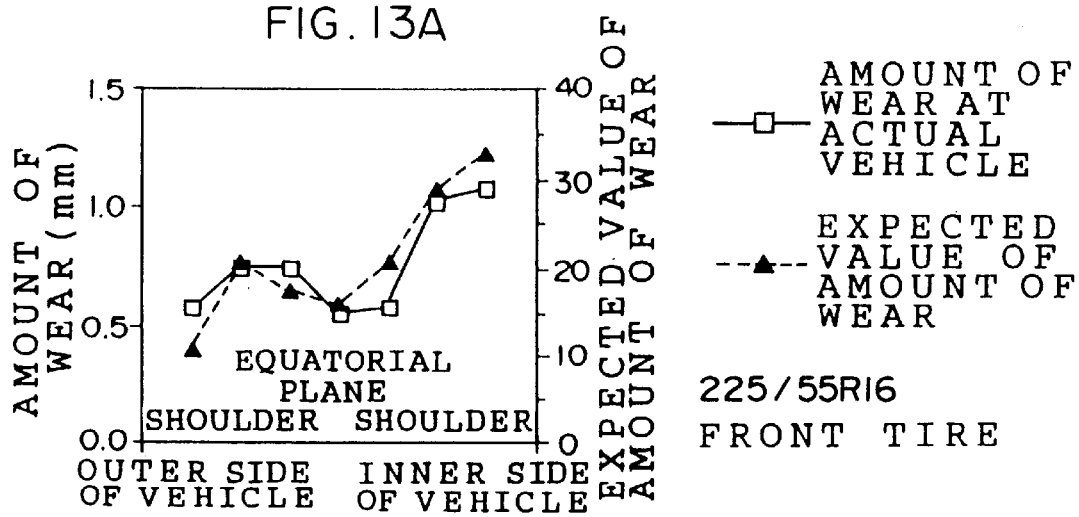
FIG. 13A shows a graph exhibiting the relation between the expected value of the tire wear life and the amount of wear of a tire attached to an actual vehicle in the transverse direction of the tread. (A case in which a tire of a size 225/55R16 was used as a front tire) according to the first embodiment
Figure 13B:
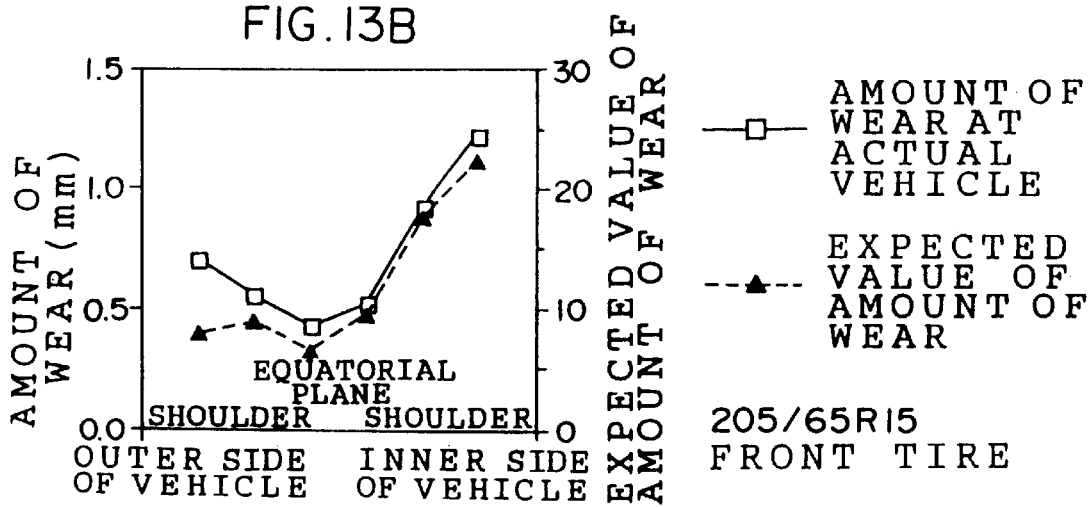
FIG. 13B shows a graph exhibiting the relation between the expected value of the tire wear life and the amount of wear of a tire attached to an actual vehicle in the transverse direction of the tread. (A case in which a tire of a size 205/65R15 was used as a front tire) according to the first embodiment.
Figure 13C:
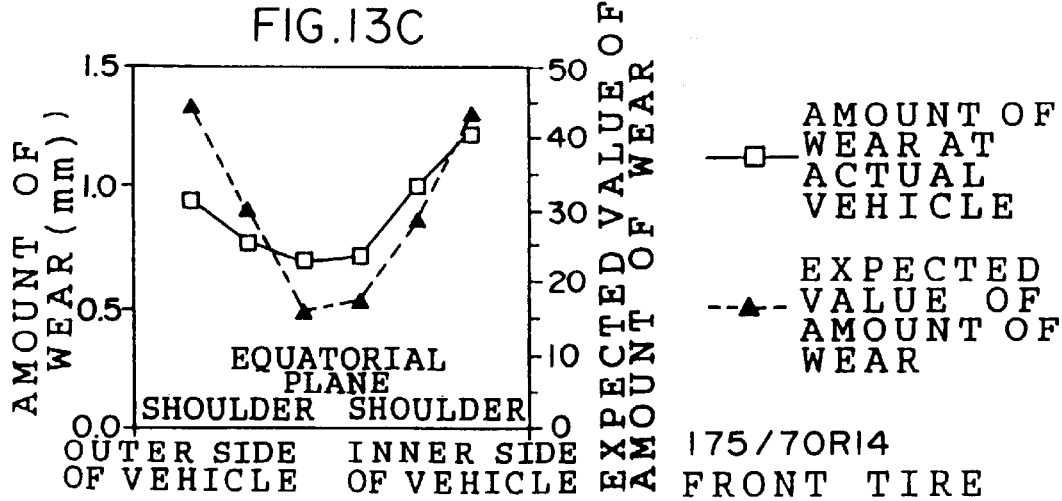
FIG. 13C shows a graph exhibiting the relation between the expected value of the tire wear life and the amount of wear of a tire attached to an actual vehicle in the transverse direction of the tread. (A case in which a tire of a size 175/70R14 was used as a front tire) according to the first embodiment.

In FIGS. 13A to 13C, the expected values of the amount of wear (obtained in accordance with the above procedures, particularly the procedures including step 205) at 6 or 7 sites of estimation in the region from the shoulder portion at the left end portion of the tire tread in the transverse direction to the shoulder portion at the right end portion of the tire tread in the transverse direction with 3 types of tires and the amount of wear at the same 6 or 7 positions obtained by the actual vehicle test are shown together.

FIG. 13A shows the results obtained using a tire having a size 225/55R16 as a front tire tread of a vehicle. FIG. 13B shows the results obtained using a tire having a size 205/65R15 as a front tire of a vehicle. FIG. 13C shows the results obtained using a tire having a size 175/70R14 as a front tire of a vehicle.

As shown in the figures, the irregular wear in the transverse direction of the tire tread can be estimated accurately from the distribution of the expected values of the amount of wear at the sites of estimation in accordance with the method of the present embodiment.

As described in detail in the above, in the method for estimating a tire wear life of the present embodiment, the friction energies Ewf and Ewa are used as the factors for estimating the tire wear life in addition to the friction energies Ews, Ewd and Ewb in the same manner as that in the first embodiment. Therefore, the tire wear life can be estimated more accurately in comparison with the estimation in accordance with Schallamach's formula in which rigidities in the direction of driving, in the direction of braking and in the transverse direction alone are taken into consideration.

The rubber index Gi measured under a severity (a slip ratio) approximately the same as the severity in the actual use of the tire is used for the estimation. Therefore, the tire wear life can be estimated more accurately in comparison with the estimation using the wear resistance index obtained by the conventional Lambourn abrasion test specified in Japanese Industrial Standard K 6264.

In the method for estimating a tire wear life of the present embodiment, the friction energies Ews, Ewd and Ewb described in the first embodiment are obtained on the basis of the RMS values of the distribution of acceleration in the transverse direction at the center of gravity position of a vehicle and the distribution of acceleration in the longitudinal direction at the center of gravity position of the vehicle in the actual use of the vehicle, and thus the friction energies reflect the input forces in the actual use of the vehicle. Accordingly, the tire wear life can be estimated more accurately in comparison with the estimation in accordance with the method of tire wear life estimation described in the first embodiment.

In the method for estimating a tire wear life of the present embodiment, the friction energy of the tire Ews under application of a side force is divided into the friction energy of the tire Ews+ in the rightward turn of the vehicle and the friction energy of the tire Ews− in the left turn of the vehicle on the basis of the Ackerman characteristics and the toe angle and each friction energy is separately obtained. The friction energy Ews is then obtained as the sum of the friction energy Ews+ and the friction energy Ews−.

Therefore, the friction energy Ews much closer to the friction energy which would be obtained in the actual use of the vehicle can be obtained in the present embodiment in comparison with the estimation of the friction energy Ews without using the Ackerman characteristics or the toe angle.

Moreover, in the method for estimating a tire wear life of the present embodiment, the expected value Ti of the tire wear life (and the expected value of the amount of wear, where necessary) is obtained at a plurality of positions in the transverse direction of the tire tread and thus the distribution of the tire wear life (or the amount of wear) in the transverse direction of the tire tread (that is, irregular wear) can be estimated.

In the above description of the present embodiment, the apparatus 10 for measuring the parameters required for the computation of the friction energies generated at the road-contacting portion of the tire tread (shown in FIG. 10) described in the specification of JP-A 7-63658 is used for the measurement of the friction energies Ewf and Ewa. However, the present invention is not limited to this case. For example, as described in the first embodiment, the Tire Pressure and Slip Plate, an apparatus for measuring the road-contacting pressure and displacement manufactured by PRECISION MEASUREMENT Co., U.S. A., may be used. This apparatus is used for measurement of the friction energy in "A trial for laboratory evaluation of tire wear" by YOKOHAMA RUBBER Co., Ltd., reported in the preprints of the fall lecture meeting of Japanese Automotive Engineers in 1982.

In the above description of the present embodiment, the exponents ns1, ns2, nd and nb are fixed at the value of 2 and each friction energy is measured a plurality of times by each time applying a given value of the input force. Then, the undetermined coefficients S1, S2, D and B in formulae (16) to (19) are obtained from the input forces and the measured friction energies by the reversed use of formulae (16) to (19). However, the present invention is not limited to this case. In another example, each friction energy may be measured a plurality of times by each time applying a given value of the input force without fixing the exponents ns1, ns2, nd and nb to any particular values, so that approximate values of the undetermined coefficients S1, S2, D and B and exponents ns1, ns2, nd and nb can be obtained from the relation between the input forces and the friction energies in accordance with the least square method or the deviation area method.

The tire wear life can be estimated more accurately in accordance with the latter method in comparison with the method in which the exponents ns1, ns2, nd and nb are set at a fixed value.

In the above description of the present embodiment, the expected value of the tire wear life or the expected amount of wear is calculated separately at each of the plurality of sites of estimation. However, the present invention is not limited to this case. After the friction energies are measured at the sites of estimation, the expected values of the tire wear life or the expected amounts of wear may be calculated simultaneously. This characteristic is also applied to the following second and third embodiments.

In the above description of the present embodiments, the rubber index Gi is obtained using the abrasion test apparatus whose main portion is shown in FIG. 6. However, the present invention is not limited to this case. Any apparatus which can measure the condition of wear at a low severity of about 0.5 to 5%, i.e., at the same severity as the severity in the actual use of the tire, can be used. For example, an abrasion tester of elastomers described in the specification of Japanese Patent Application No. 9-7168 may be used. This characteristic is also applied to the following second and third embodiments.

In the above description of the present embodiments, in the measurement of the rubber index Gi, the effective dynamic load radius (the effective radius under dynamic load) of a rubber test piece is obtained from the amount of displacement of the movable base relative to the reference position. However, the present invention is not limited to this case. Alternatively, the circumferential length of the rubber test piece is obtained and the rolling radius of the rubber test piece may be obtained from the obtained circumferential length.

More specifically, the circumferential length of a rubber test piece can be obtained as follows. A round disk having a notch at a circumferential end portion is disposed at each of the rubber test piece and the grindstone at corresponding positions. The disk disposed at the rubber test piece and the disk disposed at the grindstone rotate synchronously with the rotation of the rubber test piece and the rotation of the grindstone, respectively. A photosensor composed of a light emitting portion and a light receiving portion is disposed at each disk such that the round disk is placed between the light emitting portion and the light receiving portion and the light emitted from the light emitting portion to the light receiving portion intersects the locus of the notch formed as a result of the rotation of the round disk. The photosensor generates a pulse when the light receiving portion receives light emitted from the light emitting portion. The circumferential length of the rubber test piece is obtained from the interval between the pulses generated by the photosensor at the grindstone, the interval between pulses generated by the photosensor at the rubber test piece and the circumferential length of the grindstone. This characteristic is also applied to the following second and third embodiments.

In the above description of the present embodiments, in the measurement of the rubber index Gi, the rubber test piece is moved toward the grindstone which is fixed so that the rubber test piece is pressed against the grindstone. The present invention is not limited to this case. The rubber test piece may be pressed against the grindstone by moving the grindstone while the rubber test piece is in a fixed position or by moving both rubber test piece and grindstone. This characteristic is also applied to the following second and third embodiments.

In the above description of the present embodiments, in the measurement of the rubber index Gi, the longitudinal force is detected by the force component meter. However, the present invention is not limited to this case. The longitudinal force generated by driving may be measured by using a conventional torque meter 83. When the conventional torque meter is used, the result contains torque generated by bearings and the accuracy of measurement is inferior to the accuracy obtained using the force component meter 89. This characteristic is also applied to the following second and third embodiments.

In the above description of the present embodiments, in the measurement of the rubber index Gi, the slip ratio is adjusted by adjusting the angular speed of the rubber test piece while the angular speed of the grindstone is set at a fixed value. However, the present invention is not limited to this case. The slip ratio may be adjusted by adjusting the angular speed of the grindstone while the angular speed of the rubber test piece is set at fixed a value or by adjusting both angular speed of the grindstone and angular speed of the rubber test piece. This characteristic is also applied to the following second and third embodiments.

[The Second Embodiment]

The second embodiment of the present invention will be described in detail with reference to figures in the following. As the construction in the present embodiment is basically the same as the construction described in the first embodiment, detailed descriptions thereof are omitted.

The present embodiment is fundamentally the same as the first embodiment. However, the estimation is made by using the degree of rubber wear Wt of a tire in place of the expected tire wear life T1.

In the present embodiment, the same procedures as those in the first embodiment are conducted from the first step to the step of obtaining the length of wear in the radial direction (the wear depth) W (mm/1000 km) of a rubber test piece 4 per 1000 km.

The value of W is obtained from the measured amount of wear $W_0$ (=m1−m2) (g) in accordance with the following formula (23):

$$W = \frac{W_o \cdot 10^9}{\rho \cdot (V_d \cdot t) \cdot (2\pi R_r \cdot D)} \quad \text{formula (23)}$$

Using values obtained in accordance with formulae (22) and (23), the degree of rubber wear V is obtained as the wear depth per unit friction energy in accordance with the following formula (25):

$$V = W/ew \quad (25)$$

When the friction energy (detected by a detector similar to that of the first embodiment) of a tire which is attached to a vehicle and uses the same material as the material of the rubber test piece is represented by $ew_t$, the degree of rubber wear of a tire Wt is estimated in accordance with the following formula (26):

$$Wt = V \cdot ew_t \quad (26)$$

EXAMPLES

Rubber test pieces 4 prepared by using the formulation shown in Table 1 and having a theoretical radius Rs of 2.45 cm and a width D of 1.00 cm were examined with various patterns. The obtained results are shown in Table 2.

TABLE 1

| Formulation | Amount (phr) |
|---|---|
| SBR 1712[1] | 68.75 |

TABLE 1-continued

| Formulation | Amount (phr) |
|---|---|
| SBR 1500 | 50 |
| Carbon black N234 | 70 |
| Naphthenic oil NP24 | 7.5 |
| Stearic acid | 2 |
| Antioxidant 6PPD[2] | 2 |
| Zinc oxide | 3.5 |
| Wax[3] | 1 |
| Vulcanization accelerator DPG[4] | 0.5 |
| Vulcanization accelerator MBTS[5] | 1.0 |
| Sulfur | 1.5 |

[1] Oil extended SBR, manufactured by JSR Co., Ltd.
[2] N-(1,3-dimethylbutyl)-N'-phenyl-p-phenylenediamine
[3] SUNTIGHT, a trade name, manufactured by SEIKO KAGAKU Co., Ltd.
[4] Diphenylguanidine
[5] Dibenzothiazyldisulfide

TABLE 2-1

| S (%) | Rr (cm) | $W_0$ (g) | t (min) | ρ (g/cm³) | W (mm/ 1000 km) | $F_y-F_0$ (kgf) | $ew_1$ (kgf/cm²) |
|---|---|---|---|---|---|---|---|
| 0.5 | 2.38 | 0.0160 | 240 | 1.131 | 0.654 | 0.40 | $1.337 \times 10^{-4}$ |
| 0.5 | 2.38 | 0.0046 | 60 | 1.131 | 0.753 | 0.34 | $1.337 \times 10^{-4}$ |
| 1.0 | 2.43 | 0.00895 | 60 | 1.131 | 1.44 | 0.42 | $2.746 \times 10^{-4}$ |
| 3.0 | 2.37 | 0.0122 | 30 | 1.131 | 4.005 | 0.36 | $7.244 \times 10^{-4}$ |
| 4.5 | 2.37 | 0.0142 | 10 | 1.131 | 14.00 | 0.91 | $2.751 \times 10^{-4}$ |

TABLE 2-2

| S (%) | V | $ew_t$ (kgf/cm²) | W (mm/1000 km) |
|---|---|---|---|
| 0.5 | $4.89 \times 10^3$ | $1 \times 10^{-4}$ | 0.489 |
| 0.5 | $6.62 \times 10^3$ | $1 \times 10^{-4}$ | 0.662 |
| 1.0 | $5.24 \times 10^3$ | $1 \times 10^{-4}$ | 0.524 |
| 3.0 | $5.53 \times 10^3$ | $1 \times 10^{-4}$ | 0.553 |
| 4.5 | $5.09 \times 10^3$ | $1 \times 10^{-4}$ | 0.509 |

The Lambourn abrasion tests in accordance with the specification of Japanese Industrial Standard and in accordance with the modified DIN abrasion test were conducted using rubber test pieces prepared by using the same formulation as that used above and having the same size as those used above. The correlation coefficients between the obtained results of the tests and the results of the actual vehicle test are shown in Table 3.

TABLE 3

| | Correlation coefficient between estimation and actual vehicle test |
|---|---|
| Present embodiment | 0.98 |
| Comparative Example 1 (Lambourn abrasion test) | 0.84 |
| Comparative Example 2 (modified DIN abrasion test) | 0.90 |

As shown in Table 3, the results obtained in accordance with the method of the present embodiment accurately correspond to the results obtained by the actual vehicle test.

In the present embodiment, the longitudinal force is detected by a force component meter. However, the present embodiment is not limited to this method. The longitudinal force in driving may be measured by using a conventional torque meter. When the conventional torque meter is used, the result includes torque generated by the bearings and so on and the accuracy of the measurement is inferior to the accuracy obtained by using the force component meter 89.

In the present embodiment, the grindstone and the rubber test piece are constructed so that the grindstone and the rubber test piece can be both rotated and the grindstone and the rubber test piece are rotated in directions opposite to each other. However, the present embodiment is not limited to this construction. The surface of grindstone pressed to the rubber test piece may be flat and the rubber test piece may be moved while being rotated with respect to the grindstone. Or, the rubber test piece may be rotated by moving the grindstone. The rubber test piece may be moved while being rotated and the grindstone may be moved at the same time.

As described above, in accordance with the present embodiment, the slip ratio is set on the basis of the actual radius of the rubber test piece and thus the slip ratio can be set accurately. Specifically, the slip ratio can be set accurately in the range of 0.5 to 5% and the wear test can be conducted in the low friction energy region observed in the actual use of a vehicle. Thus, the results of the test accurately correspond to the results of the vehicle test.

In addition, the degree of rubber wear in the tire which is estimated from the degree of rubber wear of the rubber test piece made of the same material as the material used in the tire correspond accurately with the results of the actual vehicle test.

[The Third Embodiment]

The third embodiment of the method for estimating a tire wear life of the present invention will be described with reference to the flow chart shown in FIG. 10.

In step 100, a rubber test piece which is made of the same material as the material used in the tire tread portion of the tire (for example, a tire having a size 225/55R16) for estimation of the tire wear life is used as the rubber sample. The rubber index Gi of a rubber test piece of the rubber sample is obtained at a standard temperature of the atmosphere (for example, 25° C.) under a severity (a value in which the slip ratio is in the range of about 0.5 to 5%) which is approximately the same as the severity in the actual use of the tire.

In the present embodiment, to reproduce the conditions of actual use in a vehicle as much as possible, the friction energies Ews+', Ews−', Ewd' and Ewb' are measured in consideration of the camber angle, the toe angle and the load of the vehicle to which the tire is attached.

In the measurement of the friction energies Ews' (Ews+', Ews−'), Ewd' and Ewb', a camber angle, a toe angle and a load in which dynamic changes of the tire in the actual use are taken into consideration are applied to the tire. The camber angle, the toe angle and the load are obtained by the computer simulation using the vehicle model having 5 or more freedoms described above.

To provide the tire with the camber angle, the toe angle and the load obtained above, when the apparatus for measuring the parameter values required for calculating the friction energies generated at the road-contacting portion 10 shown in FIG. 7 is used as the apparatus of measurement, the tire 30 is attached to the upper portion of the tire support 54 in the apparatus 10 in a manner such that the attached tire 30 has the desired camber angle with respect to the vertical direction and the desired toe angle with respect to the direction of movement of the tire 30. In addition, the pressure of the tire 30 against the road surface 22 is adjusted by pressing the tire 30 to a converter of three force components 32 disposed on the road surface 22 so that the pressure shows the desired value. Then, the measurement is conducted.

The other details about this measurement are the same as those in the first embodiment and the detailed descriptions are omitted.

After the friction energies are measured as described above, in step 104 shown in FIG. 10, the expected value of the wear life T1 of the tire can be calculated by using the values of the rubber index Gi measured in step 100, the friction energies measured in step 102 and the groove depth NSD of the tire in formula (9). In the first embodiment, the groove depth NSD of the tire is measured in advance as the average value of the values of the groove depths measured at a plurality of positions of the tire tread portion. The friction energy Ew used in formula (9) is obtained in accordance with formula (6).

In the next step 106, the tire wear life is estimated on the basis of the expected value T1 of the tire wear life calculated in step 104. The estimation of the tire wear life can be made in various ways. For example, the expected tire wear life T1 of a tire obtained above is compared with expected wear life T1 of other tires and estimated as longer or shorter than the wear life of the other tires. As another example, a graph as shown in FIG. 4 is prepared with a reference tire in advance and the wear life of the object tire is obtained using the graph and the obtained expected value T1 of the tire wear life.

In the present embodiment of the method for estimating a tire wear life, using an input force in the transverse direction Fy+ generated during a rightward turn of the vehicle, an input force in the transverse direction Fy− generated during a leftward turn of the vehicle, a force in the forward direction Fx+ generated by the driving force, a force in the backward direction Fx− generated by the braking force, undetermined coefficients S1, S2, D and B and exponents ns1, ns2, nd and nb (ns1, ns2, nd and nb may be set at 2), the friction energy Ews+, the friction energy Ews−, the friction energy Ewd and the friction energy Ewb may be expressed by the following formulae as above described:

$$Ews+ = S1 \times Fy+^{ns1} \quad (16)$$

$$Ews- = 2 \times Fy-^{ns2} \quad (17)$$

$$Ewd = D \times Fx+^{nd} \quad (18)$$

$$Ewb = B \times FX-^{nb} \quad (19)$$

Figure 14A:
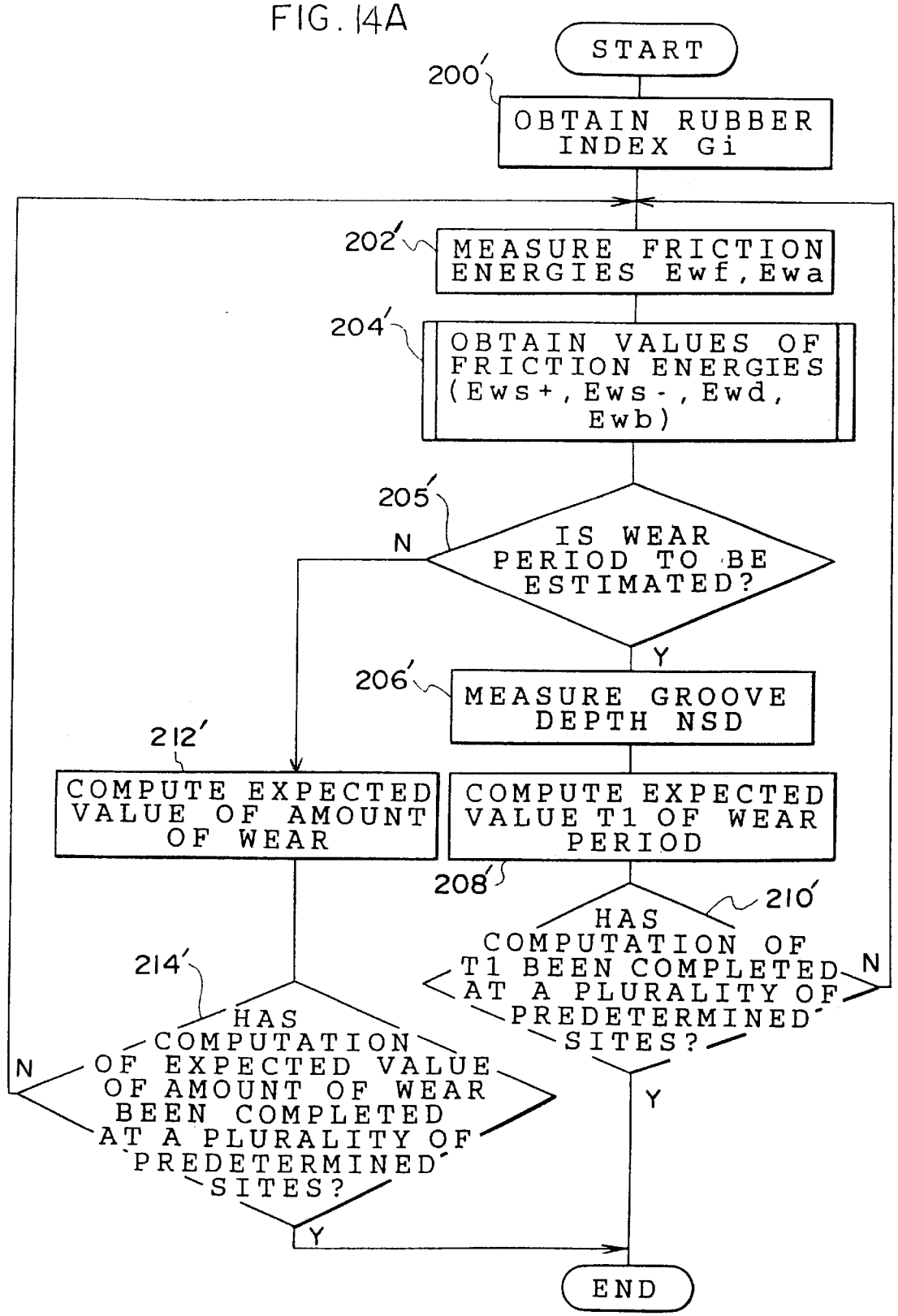
FIG. 14A shows a schematic flow chart exhibiting the procedures for estimation of the tire wear life in the first embodiment.
Figure 14B:
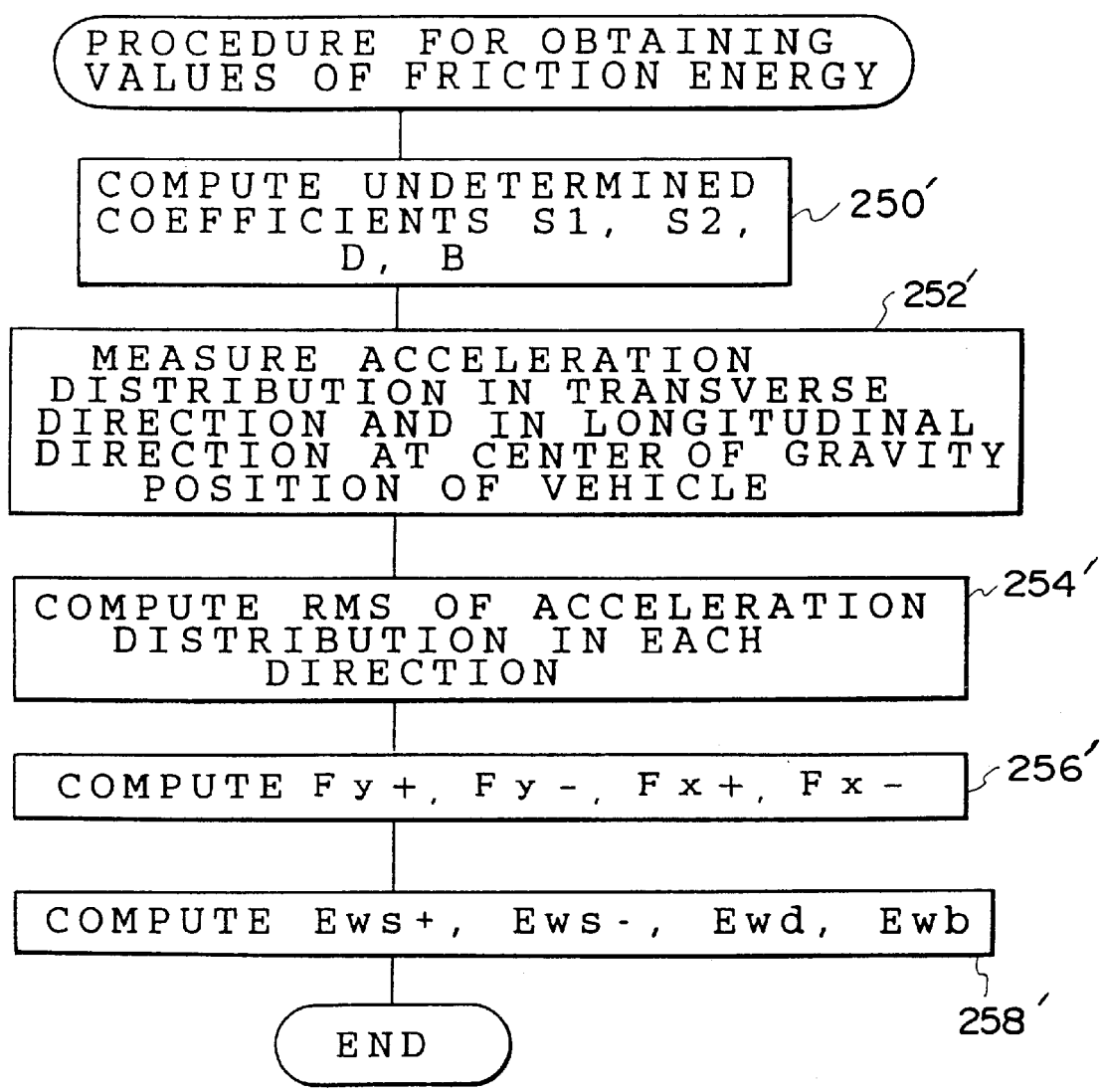
FIG. 14B shows a schematic flow chart exhibiting the procedures for obtaining the friction energies Ews+', Ews−', Ewd' and Ewb' in the first embodiment.

Referring to FIGS. 14A and 14B, at step 200', a rubber index Gi as in the same manner as step 100'. At step 202', Ewf and Ewa are obtained in the same manner as step 102'. At step 204', Ews+', the friction energy Ews−', the friction energy Ewd' and the friction energy Ewb' are obtained. Further steps are conducted in the same manner in the first embodiment. As other details are similar to those in the first embodiment, descriptions thereof are omitted.

In FIGS. 15A to 15C, the expected values of the amount of wear (obtained in accordance with the above procedures, particularly the procedures including step 205') at 6 or 7 sites of estimation in the region from the shoulder portion at the left end portion of the tire tread in the transverse direction to the shoulder portion at the right end portion of the tire tread in the transverse direction with 3 types of tires and the amount shown together. Compared to the results shown in FIGS. 13A to 13C, the estimation accuracy shown in FIGS. 15A to 15c is obviously more excellent.

As described above in detail, in accordance with the third embodiment of the method for estimating the tire wear life, the friction energy of the tire Ewf in a state of free rolling and the friction energy of the tire Ewa in a state in which the tire is given a toe angle are used as the factors for estimating the tire wear life in addition to the friction energies of the tire Ews', Ewd' and Ewb' (These parameters are dashed so that they can be distinguished from Ews, Ewd and Ewb according to the first embodiment). Therefore, the tire wear life can be estimated more accurately in comparison with the case in which the tire wear life is estimated in accordance with Schallamach's formula using rigidities in the driving direction, in the braking direction and the transverse direction alone.

Further, the rubber index Gi measured under a severity (a slip ratio) approximately the same as the severity in the actual use of the tire is used for the estimation. Therefore, the tire wear life can be estimated more accurately in comparison with the case in which the tire wear life is estimated by using the wear resistance index obtained by the conventional Lambourn abrasion test specified in Japanese Industrial Standard K 6264.

In the present embodiment of the method for estimating a tire wear life, the camber angle, the toe angle and the load which reflect the dynamic changes in the actual use of the tire are taken into consideration in the measurement of the friction energies Ews', Ewd' and Ewb'. Therefore, the tire wear life can be estimated more accurately in comparison with the estimation without considering the camber angle, the toe angle or the load.

In the present embodiment of the method for estimating a tire wear life, the tire wear life can be estimated only by the measurement of the rubber index Gi using the abrasion tester (the main portions of tester are shown in FIG. 6), and by the measurement of the friction energies using the apparatus 10 shown in FIG. 7. Therefore, a vehicle test using an actual vehicle is not necessary and the estimation can be made in a short time.

In the present embodiment, the apparatus 10 shown in FIG. 7 specifically described in the specification of JP-A 7-63658 is used for the measurement of the friction energies. However, the present invention is not limited to this case. For example, the Tire Pressure and Slip Plate, an apparatus for measuring the road-contacting pressure and displacement manufactured by PRECISION MEASUREMENT Co., U.S. A., may be used. This apparatus is used for measurement of the friction energy in "A trial on laboratory evaluation of tire wear" by YOKOHAMA RUBBER Co., Ltd. reported in the preprint for the fall lecture meeting of the Society of Japanese Automotive Engineers in 1982.

In the present embodiment, the groove depth NSD is obtained as an average of a plurality of groove depths in the tire tread portion. However, the present invention is not limited to this case. For example, the minimum value among a plurality of the groove depths may be used as the groove depth.

In the present embodiment, the tire wear life is estimated on the basis of the value obtained by multiplying the remaining groove depth remaining before the groove depth reaches the limit for disposal of the tire by the product of the rubber index Gi with the reciprocal of the friction energy Ew' (1/Ew'), i.e., Gi/Ew'. However, the present invention is not limited to this case. For example, a value close to the expected value of the tire wear life may be obtained using the product Gi/Ew' alone.

In the present embodiment, the friction energies expressed as values per unit area and unit distance of driving standardized by using the rolling radius of the tire are used. However, the present invention is not limited to this case. It is not necessary that the friction energies are expressed as values standardized by using the rolling radius of the tire. In this case, the friction energies are expressed by the unit of kgf/cm.

What is claimed is:

1. A method for estimating a tire wear life which comprises:

a step of obtaining a friction energy value of the tire Ewf in free rolling, a friction energy value of the tire Ewa in a state in which the tire is provided with a toe angle, a friction energy value of the tire Ews in a state in which a side force is applied to the tire, a friction energy value of the tire Ewd in a state in which a driving force is applied to the tire, and a friction energy value of the tire Ewb in a state in which a braking force is applied to the tire;

a step of obtaining a friction energy value ew of a rubber sample made of the same material as the material used in a tire tread portion under a severity approximately the same as the severity in actual use of the tire and a wear depth W per given driving distance;

a step of obtaining a rubber index Gi which is a value obtained by dividing the friction energy ew by the wear depth W, i.e., ew/W, and a friction energy Ew expressed by the following formula:

$$Ew=Ewf+Ewa+Ews+Ewb+Ewd$$

and a step of estimating the tire wear life on the basis of a value including a product of the rubber index Gi and a reciprocal of Ew (1/Ew), i.e., Gi/Ew.

2. A method for estimating a tire wear life according to claim 1, wherein the value containing the product Gi/Ew is a value selected from the product Gi/Ew or a value obtained by multiplying the product Gi/Ew by a remaining groove depth remaining before the groove depth reaches a limit for disposal of the tire.

3. A method for estimating a tire wear life according to claim 1, which further comprises:

a step of expressing the friction energy Ews, the friction energy Ewd and the friction energy Ewb, using an input force in a transverse direction Fy, a force in a forward direction Fx+ generated by the driving force, a force in a backward direction Fx− generated by the braking force, undetermined coefficients S, D and B and exponents ns, nd and nb, by the following formulae:

$$Ews=S \times Fy^{ns}$$

$$Ewd=D \times Fx+^{nd}$$

$$Ewb=B \times FX-^{nb}$$

a step of determining the undetermined coefficients S, D and B and the exponents ns, nd and nb in advance on the basis of values of the friction energy Ews, the friction energy Ewd and the friction energy Ewb measured under application of a given value of the input force in the transverse direction Fy, a given value of the force in the forward direction Fx+ and a given value of the force in the backward direction Fx−, respectively;

a step of determining values of the input force in the transverse direction Fy, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews, the friction energy Ewd and the friction energy Ewb on the basis of the determined values of the input force in the transverse direction Fy, the force in the forward direction Fx+ and the force in the backward direction Fx− in accordance with the above formulae in which the coefficients and the exponents have been determined.

4. A method for estimating a tire wear life according to claim 2, which further comprises:

a step of expressing the friction energy Ews, the friction energy Ewd and the friction energy Ewb, using an input force in a transverse direction Fy, a force in a forward direction Fx+ generated by the driving force, a force in a backward direction Fx− generated by the braking force, undetermined coefficients S, D and B and exponents ns, nd and nb, by the following formulae:

$$Ews=S \times Fy^{ns}$$

$$Ewd=D \times Fx+^{nd}$$

$$Ewb=B \times FX-^{nb}$$

a step of determining the undetermined coefficients S, D and B and the exponents ns, nd and nb in advance on the basis of values of the friction energy Ews, the friction energy Ewd and the friction energy Ewb measured under application of a given value of the input force in the transverse direction Fy, a given value of the force in the forward direction Fx+ and a given value of the force in the backward direction Fx−, respectively;

a step of determining values of the input force in the transverse direction Fy, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews, the friction energy Ewd and the friction energy Ewb on the basis of the determined values of the input force in the transverse direction Fy, the force in the forward direction Fx+ and the force in the backward direction Fx− in accordance with the above formulae in which the coefficients and the exponents have been determined.

5. A method for estimating a tire wear life according to claim 1, which further comprises:

a step of expressing the friction energy Ews, the friction energy Ewd and the friction energy Ewb, using an input force in a transverse direction Fy, a force in a forward direction Fx+ generated by the driving force, a force in a backward direction Fx− generated by the braking force, undetermined coefficients S, D and B and exponents ns, nd and nb, by the following formulae:

$$Ews=S \times Fy^{ns}$$

$$Ewd=D \times Fx+^{nd}$$

$$Ewb=B \times FX-^{nb}$$

a step of setting each of the exponents ns, nd and nb at a specific value between 1.5 and 3 and determining the undetermined coefficients S, D and B in advance on the basis of values of the friction energy Ews, the friction energy Ewd and the friction energy Ewb measured under application of an input force in the transverse direction Fy, a force in the forward direction Fx+ and a force in the backward direction Fx−, respectively;

a step of determining values of the input force in the transverse direction Fy, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews, the friction energy Ewd and the friction energy Ewb on the basis of the determined values of the input force in the transverse direction Fy, the force in the forward direction Fx+ and the force in the backward direction Fx− in accordance with the above formulae in which the coefficients and the exponents have been determined.

6. A method for estimating a tire wear life according to claim 2, which further comprises:

a step of expressing the friction energy Ews, the friction energy Ewd and the friction energy Ewb, using an input force in a transverse direction Fy, a force in a forward direction Fx+ generated by the driving force, a force in a backward direction Fx− generated by the braking force, undetermined coefficients S, D and B and exponents ns, nd and nb, by the following formulae:

$Ews = S \times Fy^{ns}$ $Ewd = D \times Fx+^{nd}$ $Ewb = B \times FX-^{nb}$ a step of setting each of the exponents ns, nd and nb at a specific value between 1.5 and 3 and determining the undetermined coefficients S, D and B in advance on the basis of values of the friction energy Ews, the friction energy Ewd and the friction energy Ewb measured under application of an input force in the transverse direction Fy, a force in the forward direction Fx+ and a force in the backward direction, respectively Fx−;

a step of determining values of the input force in the transverse direction Fy, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews, the friction energy Ewd and the friction energy Ewb on the basis of the determined values of the input force in the transverse direction Fy, the force in the forward direction Fx+ and the force in the backward direction Fx− in accordance with the above formulae in which the coefficients and the exponents have been determined.

7. A method for estimating a tire wear life according to claim 1, which further comprises:

a step of dividing the friction energy Ews into a friction energy Ews+ generated in a rightward turn of a vehicle to which the tire is mounted and a friction energy Ews− generated in a leftward turn of the vehicle to which the tire is mounted on the basis of an Ackerman characteristic and the toe angle of the vehicle and obtaining each of the friction energy Ews+ and the friction energy Ews−; and a step of obtaining the friction energy Ews as a sum of the friction energy Ews+ and the friction energy Ews−, i.e., Ews++Ews−.

8. A method for estimating a tire wear life according to claim 2, which further comprises:

a step of dividing the friction energy Ews into a friction energy Ews+ generated in a rightward turn of a vehicle to which the tire is mounted and a friction energy Ews− generated in a leftward turn of the vehicle to which the tire is mounted on the basis of an Ackerman characteristic and the toe angle of the vehicle and obtaining each of the friction energy Ews+ and the friction energy Ews−; and a step of obtaining the friction energy Ews as a sum of the friction energy Ews+ and the friction energy Ews−, i.e., Ews++Ews−.

9. A method for estimating a tire wear life according to claim 7, which further comprises:

a step of expressing a friction energy Ews+, a friction energy Ews−, the friction energy Ewd and the friction energy Ewb, using an input force in a transverse direction Fy+ generated in a rightward turn of a vehicle, an input force in a transverse direction Fy− generated in a leftward turn of the vehicle, a force in a forward direction Fx+ generated by the driving force, a force in a backward direction Fx− generated by the braking force, undetermined coefficients S1, S2, D and B and exponents ns1, ns2, nd and nb, by the following formulae:

$Ews+ = S1 \times Fy+^{ns1}$ $Ews- = S2 \times Fy-^{ns2}$ $Ewd = D \times Fx+^{nd}$ $Ewb = B \times FX-^{nb}$ a step of determining the undetermined coefficients S1, S2, D and B and the exponents ns1, ns2, nd and nb in advance on the basis of values of the friction energy Ews+, the friction energy Ews−, the friction energy Ewd and the friction energy Ewb measured under application of a given value of the input force in the transverse direction Fy+, a given value of the input force in the transverse direction Fy−, a given value of the force in the forward direction Fx+ and a given value of the force in the backward direction Fx−, respectively;

a step of determining values of the input force in the transverse direction Fy+, the input force in the transverse direction Fy−, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews+, the friction energy Ews−, the friction energy Ewd and the friction energy Ewb on the basis of the determined values of the input force in the transverse direction Fy+, the input force in the transverse direction Fy−, the force in the forward direction Fx+ and the force in the backward direction Fx− in accordance with the above formulae in which the coefficients and the exponents have been determined.

10. A method for estimating a tire wear life according to claim 8, which further comprises:

a step of expressing a friction energy Ews+, a friction energy Ews−, the friction energy Ewd and the friction energy Ewb, using an input force in a transverse direction Fy+ generated in rightward turn of a vehicle, an input force in a transverse direction Fy− generated in leftward turn of the vehicle, a force in a forward direction Fx+ generated by the driving force, a force in a backward direction Fx− generated by the braking force, undetermined coefficients S1, S2, D and B and exponents ns1, ns2, nd and nb, by the following formulae:

$$Ews+ = S1 \times Fy+^{ns1}$$

$$Ews- = S2 \times Fy-^{ns2}$$

$$Ewd = D \times Fx+^{nd}$$

$$Ewb = B \times FX-^{nb}$$

a step of determining the undetermined coefficients S1, S2, D and B and the exponents ns1, ns2, nd and nb in advance on the basis of values of the friction energy Ews+, the friction energy Ews−, the friction energy Ewd and the friction energy Ewb measured under application of a given value of the input force in the transverse direction Fy+, a given value of the input force in the transverse direction Fy−, a given value of the force in the forward direction Fx+ and a given value of the force in the backward direction Fx−, respectively;

a step of determining values of the input force in the transverse direction Fy+, the input force in the transverse direction Fy−, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews+, the friction energy Ews−, the friction energy Ewd and the friction energy Ewb on the basis of the determined values of the input force in the transverse direction Fy+, the input force in the transverse direction Fy−, the force in the forward direction Fx+ and the force in the backward direction Fx− in accordance with the above formulae in which the coefficients and the exponents have been determined.

11. A method for estimating a tire wear life according to claim 7, which further comprises:

a step of expressing a friction energy Ews+, a friction energy Ews−, the friction energy Ewd and the friction energy Ewb, using an input force in a transverse direction Fy+ generated in rightward turn of a vehicle, an input force in a transverse direction Fy− generated in leftward turn of the vehicle, a force in a forward direction Fx+ generated by the driving force, a force in a backward direction Fx− generated by the braking force, undetermined coefficients S1, S2, D and B and exponents ns1, ns2, nd and nb, by the following formulae:

$$Ews+ = S1 \times Fy+^{ns1}$$

$$Ews- = S2 \times Fy-^{ns2}$$

$$Ewd = D \times Fx+^{nd}$$

$$Ewb = B \times FX-^{nb}$$

a step of setting each of exponents ns1, ns2, nd and nb at a specific value between 1.5 and 3 and determining the undetermined coefficients S1, S2, D and B in advance on the basis of values of the friction energy Ews+, the friction energy Ews−, the friction energy Ewd and the friction energy Ewb measured under application of a given value of the input force in the transverse direction Fy+, a given value of the input force in the transverse direction Fy−, a given value of the force in the forward direction Fx+ and a given value of the force in the backward direction Fx−, respectively;

a step of determining values of the input force in the transverse direction Fy+, the input force in the transverse direction Fy−, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews+, the friction energy Ews−, the friction energy Ewd and the friction energy Ewb on the basis of the determined values of the input force in the transverse direction Fy+, the input force in the transverse direction Fy−, the force in the forward direction Fx+ and the force in the backward direction Fx− in accordance with the above formulae in which the coefficients and the exponents have been determined.

12. A method for estimating a tire wear life according to claim 8, which further comprises:

a step of expressing a friction energy Ews+, a friction energy Ews−, the friction energy Ewd and the friction energy Ewb, using an input force in a transverse direction Fy+ generated in rightward turn of a vehicle, an input force in a transverse direction Fy− generated in leftward turn of the vehicle, a force in a forward direction Fx+ generated by the driving force, a force in a backward direction Fx− generated by the braking force, undetermined coefficients S1, S2, D and B and exponents ns1, ns2, nd and nb, by the following formulae:

$$Ews+ = S1 \times Fy+^{ns1}$$

$$Ews- = S2 \times Fy-^{ns2}$$

$$Ewd = D \times Fx+^{nd}$$

$$Ewb = B \times FX-^{nb}$$

a step of setting each of exponents ns1, ns2, nd and nb at a specific value between 1.5 and 3 and determining the undetermined coefficients S1, S2, D and B in advance on the basis of values of the friction energy Ews+, the friction energy Ews−, the friction energy Ewd and the friction energy Ewb measured under application of a given value of the input force in the transverse direction Fy+, a given value of the input force in the transverse direction Fy−, a given value of the force in the forward direction Fx+ and a given value of the force in the backward direction Fx−, respectively;

a step of determining values of the input force in the transverse direction Fy+, the input force in the transverse direction Fy−, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews+, the friction energy Ews−, the friction energy Ewd and the friction energy Ewb on the basis of the determined values of the input force in the transverse direction Fy+, the input force in the transverse direction Fy−, the force in the forward direction Fx+ and the force in the backward direction Fx− in accordance with the above formulae in which the coefficients and the exponents have been determined.

13. A method for estimating a tire wear life according to claim 1, wherein the tire wear life is estimated at a plurality of portions of the tire.

14. A method for estimating a tire wear life according to claim 2, wherein the tire wear life is estimated at a plurality of portions of the tire.

15. A method for estimating a tire wear life according to claim 1, wherein the friction energy Ew is expressed as a value per unit area and unit distance of driving standardized using a rolling radius of the tire.

16. A method for estimating a tire wear life according to claim 2, wherein the friction energy Ew is expressed as a value per unit area and unit distance of driving standardized using a rolling radius of the tire.

17. A method for estimating a tire wear life according to claim 1, wherein, on the basis of the measured value of the rubber index Gi and the friction energy Ew, an expected value of an amount of wear is expressed by a formula:

expected value of an amount of wear=Ew/Gi.

18. A method for estimating a tire wear life according to claim 7, wherein, on the basis of a measured value of the rubber index Gi and the friction energies Ewf, Ewa, Ews+, Ews−, Ewd, and Ewb, an expected value of an amount of wear is expressed by a formula:

expected value of an amount of wear={(Ewf)+(Ewa)+(Ews+)+(Ews−)+(Ewd)+(Ewb)}/Gi

=Ew/Gi.

19. A method for estimating a tire wear life according to claim 8, wherein, on the basis of a measured value of the rubber index Gi and the friction energies Ewf, Ewa, Ews+, Ews−, Ewd, and Ewb, an expected value of an amount of wear is expressed by a formula:

expected value of an amount of wear={(Ewf)+(Ewa)+(Ews+)+(Ews−)+(Ewd)+(Ewb)}/Gi

=Ew/Gi.

20. A method for estimating a tire wear life which comprises:

a step of pressing at least one of a road surface simulation member and a rotatable rubber test piece against the other of the road surface simulation member and the rotatable rubber test piece such that the road surface simulation member and the rubber test piece are in a pressed state, and driving the rubber test piece to rotate;

a step of measuring a radius (Rr) of the rubber test piece at the side thereof which presses the side of pressing the road surface simulation member when the rubber test piece is pressed against the road surface simulation member and rotated and/or when the road surface simulation member is pressed against the rubber test piece;

a step of adjusting, on the basis of the measured radius of the rubber test piece, the slip rate of the rubber test piece such that the rubber test piece is rotated at a slip rate which is in the range of 0.5% to 5%;

a step of rotating the rubber test piece freely with respect to the road surface simulation member;

a step of measuring a longitudinal force when the rubber test piece is rotated at a slip rate which is in the range of 0.5% to 5% and a longitudinal force when the rubber test piece is rotated freely with respect to the road surface simulation member, the longitudinal force being defined as a force in a direction tangential to the plane of contact between the road surface simulation member and the rubber test piece; and a step of obtaining a degree of rubber wear (V) from values including a friction energy (ew) obtained on the basis of each of the detected longitudinal forces and the slip rate.

21. A method for estimating a tire wear life according to claim 20, further comprising:

a step of obtaining a mass value of the rubber test piece before the rubber test piece is rotated at the slip rate;

a step of obtaining a mass value of the rubber test piece after the rubber test piece is rotated at the slip rate; and a step of computing the degree of rubber wear (V) as a wear depth in the radial direction per unit friction energy (W/ew) using a wear depth in the radial direction (W) and the friction energy (ew), the wear depth in the radial direction (W) being obtained from an amount of wear of the rubber test piece ($W_0$), the density of the rubber test piece ($\rho$), and the total length (A) over which the road surface simulation member contacts the rubber test piece in a pressed state when the rubber test piece is rotated at the slip rate for a predetermined time, the amount of wear of the rubber test piece ($W_0$) being obtained on the basis of the measured mass value of the rubber test piece before the rubber test piece is rotated at the slip rate and the measured mass value of the rubber test piece after the rubber test piece is rotated at the slip rate.

22. A method for estimating a tire wear life according to claim 21, further comprising:

a step of obtaining a friction energy ($ew_t$) of a tire which is mounted onto a vehicle and formed of the same material as the material of the rubber test piece; and a step of obtaining a degree of rubber wear of the tire (Wt) on the basis of the friction energy of the tire ($ew_t$) and the degree of rubber wear (V).

23. A method for estimating a tire wear life which comprises:

a step of obtaining a friction energy value of the tire Ewf in free rolling, a friction energy of the tire Ewa in a state in which the tire is provided with a toe angle;

a step of obtaining a friction energy value of the tire Ews' in a state in which a side force is applied to the tire, a friction energy of the tire Ewd' in a state in which a driving force is applied to the tire, and a friction energy of the tire Ewb' in a state in which a braking force is applied to the tire, said friction energy values Ews', Ewd', Ewb' being each obtained in a state in which the camber angle, the toe angle and the load are provided in consideration of the condition changing between a static state and a dynamic state when the tire is used;

a step of obtaining a friction energy vasue ew of a rubber sample made of the same material as the material used in a tire tread portion under a seventy approximately the same as the severity in actual use of the tire and a wear depth W per given driving distance;

a step of obtaining a rubber index Gi which is a value obtained by dividing the friction energy ew by the wear depth W, i.e., ew/W, and a friction energy Ew' expressed by the following formula:

$$Ew'=Ewf+Ewa+Ews'+Ewb'+Ewd'$$

and a step of estimating the tire wear life on the basis of a value including a product of the rubber index Gi and a reciprocal of Ew (1/Ew), i.e., Gi/Ew.

24. A method for estimating a tire wear life according to claim 23, which further comprises:

a step of expressing the friction energy Ews', the friction energy Ewd' and the friction energy Ewb', using an input force in a transverse direction Fy, a force in a forward direction Fx+ generated by the driving force, a force in a backward direction Fx− generated by the braking force, undetermined coefficients S, D and B and exponents ns, nd and nb, by the following formulae;

$$Ews'=S \times Fy^{ns}$$

$$Ewd'=D \times Fx+^{nd}$$

$$Ewb'=B \times FX-^{nb}$$

a step of determining the undetermined coefficients S, D and B and the exponents ns, nd and nb in advance on the basis of values of the friction energy Ews', the friction energy Ewd' and the friction energy Ewb' measured under application of a given value of the input force in the transverse direction Fy, a given value of the force in the forward direction Fx+ and a given value of the force in the backward direction Fx−, respectively;

a step of determining values of the input force in the transverse direction Fy, the force in the forward direction Fx+ and the force in the backward direction Fx—on the basis of RMS value of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews', the friction energy Ewd' and the friction energy Ewb' on the basis of the determined values of the input force in the transverse direction Fy, the force in the forward direction Fx+ and the force in the backward direction Fx− in accordance with the above formulae in which the coefficients and the exponents have been determined.

25. A method for estimating a tire wear life according to claim 23, which further comprises:

a step of expressing the friction energy Ews', the friction energy Ewd' and the friction energy Ewb', using an input force in a transverse direction Fy, a force in a forward direction Fx+ generated by the driving force, a force in a backward direction Fx− generated by the braking force, undetermined coefficients S, D and B and exponents ns, nd and nb, by the following formulae:

$$Ews'=S \times Fy^{ns}$$

$$Ewd'=D \times Fx+^{nd}$$

$$Ewb'=B \times FX-^{nb}$$

a step of setting each of the exponents ns, nd and nb at a specific value between 1.5 and 3 and determining the undetermined coefficients S, D and B in advance on the basis of values of the friction energy Ews', the friction energy Ewd' and the friction energy Ewb' measured under application of an input force in the transverse direction Fy, a force in the forward direction Fx+ and a force in the backward direction Fx−, respectively;

a step of determining values of the input force in the transverse direction Fy, the force in the forward direction Fx+ and the force in the backward direction Fx− on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews', the friction energy Ewd' and the friction energy Ewb' on the basis of the determined values of the input force in the transverse direction Fy, the force in the forward direction Fx+ and the force in the backward direction Fx− in accordance with the above formulae in which the coefficients and the exponents have been determined.

26. A method for estimating a tire wear life according to claim 23, which further comprises;

a step of dividing the friction energy Ews' into a friction energy Ews+' generated in a rightward turn of a vehicle to which the tire is mounted and a friction energy Ews−' generated in a leftward turn of the vehicle to which the tire is mounted on the basis of an Ackerman characteristic and the toe angle of the vehicle and obtaining each of the friction energy Ews+' and the friction energy Ews−'; and a step of obtaining the friction energy Ews' as a sum of the friction energy Ews+' and the friction energy Ews−', i.e., Ews+'+Ews−'.

27. A method for estimating a tire wear life according to claim 23, wherein the tire wear life is estimated at a plurality of portions of the tire.

28. A method for estimating a tire wear life according to claim 23, wherein the friction energy Ew' is expressed as a value per unit area and unit distance of driving standardized using a rolling radius of the tire.

29. A method or estimating a tire wear life according to claim 23, wherein, on the basis of the measured value of the rubber index Gi and the friction energy Ew', an expected value of an amount of wear is expressed by a formula:

$$\text{expected value of an amount of wear}=Ew'/Gi.$$

30. A method for estimating a tire wear life according to claim 26, which further comprises:

a step of expressing a friction energy Ews+', a friction energy Ews−', the friction energy Ewd' and the friction energy Ewb', using an input force in a transverse direction Fy+ generated in a rightward turn of a vehicle, an input force in a transverse direction Fy− generated in a leftward turn of the vehicle, a force in a forward direction Fx+ generated by the driving force, a force in a backward direction Fx− generated by the braking force, undetermined coefficients S1, S2, D and B and exponents ns1, ns2, nd and nb, by the following formulae:

$$Ews+' = S1 \times Fy+^{ns1}$$

$$Ews-' = S2 \times Fy-^{ns2}$$

$$Ewd' = D \times Fx+^{nd}$$

$$Ewb' = B \times FX-^{nb}$$

a step of determining the undetermined coefficients S1, S2, D and B and the exponents ns1, ns2, nd and nb in advance on the basis of values of the friction energy Ews+', the friction energy Ews-', the friction energy Ewd' and the friction energy Ewb' measured under application of a given value of the input force in the transverse direction Fy+, a given value of the input force in the transverse direction Fy-, a given value of the force in the forward direction Fx+ and a given value of the force in the backward direction Fx-, respectively;

a step of determining values of the input force in the transverse direction Fy+, the input force in the transverse direction Fy-, the force in the forward direction Fx+ and the force in the backward direction Fx- on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews+', the friction energy Ews-', the friction energy Ewd' and the friction energy Ewb' on the basis of the determined values of the input force in the transverse direction Fy+, the input force in the transverse direction Fy-, the force in the forward direction Fx+ and the force in the backward direction Fx- in accordance with the above formulae in which the coefficients and the exponents have been determined.

31. A method for estimating a tire wear life according to claim 26, which further comprises:

a step of expressing a friction energy Ews+', a friction energy Ews-', the friction energy Ewd' and the friction energy Ewb', using an input force in a transverse direction Fy+ generated in rightward turn of a vehicle, an input force in a transverse direction Fy- generated in leftward turn of the vehicle, a force in a forward direction Fx+ generated by the driving force, a force in a backward direction Fx- generated by the braking force, undetermined coefficients S1, S2, D and B and exponents ns1, ns2, nd and nb, by the following formulae:

$$Ews+' = S1 \times Fy+^{ns1}$$

$$Ews-' = S2 \times Fy-^{ns2}$$

$$Ewd' = D \times Fx+^{nd}$$

$$Ewb' = B \times FX-^{nb}$$

a step of setting each of exponents ns1, ns2, nd and nb at a specific value between 1.5 and 3 and determining the undetermined coefficients S1, S2, D and B in advance on the basis of values of the friction energy Ews+', the friction energy Ews-', the friction energy Ewd' and the friction energy Ewb' measured under application of a given value of the input force in the transverse direction Fy+, a given value of the input force in the transverse direction Fy-, a given value of the force in the forward direction Fx+ and a given value of the force in the backward direction Fx-, respectively;

a step of determining values of the input force in the transverse direction Fy+, the input force in the transverse direction Fy-, the force in the forward direction Fx+ and the force m the backward direction Fx- on the basis of RMS values of the distribution of acceleration in a transverse direction at a center of gravity position of a vehicle and the distribution of acceleration in a longitudinal direction at a center of gravity position of the vehicle in actual use of the vehicle; and a step of obtaining the friction energy Ews+', the friction energy Ews-', the friction energy Ewd' and the friction energy Ewb' on the basis of the determined values of the input force in the transverse direction Fy+, the input force in the transverse direction Fy-, the force in the forward direction Fx+ and the force in the backward direction Fx- in accordance with the above formulae in which the coefficients and the exponents have been determined.

32. A method for estimating a tire wear life according to claim 26, wherein, on the basis of a measured value of the rubber index Gi and the friction energies Ewf, Ewa, Ews+', Ews-', Ewd', and Ewb', an expected value of an amount of wear is expressed by a formula:

expected value of an amount of wear $= \{(Ewf)+(Ewa)+(Ews+')+(Ews-')+(Ewd')+(Ewb')\}/Gi$ $= Ew'/Gi.$

* * * * *